(12) United States Patent
Hermans et al.

(10) Patent No.: US 9,817,947 B2
(45) Date of Patent: Nov. 14, 2017

(54) METHOD AND APPARATUS FOR MANAGING REMOTE DEVICES AND ACCESSING REMOTE DEVICE INFORMATION

(71) Applicant: ZIH Corp., Lincolnshire, IL (US)

(72) Inventors: Sebastiaan Antonius Hendrikus Maria Hermans, Alphen aan den Rijn (NL); Euro Beinat, Amsterdam (NL)

(73) Assignee: ZIH Corp., Lincolnshire, IL (US)

( * ) Notice: Subject to any disclaimer, the term of this patent is extended or adjusted under 35 U.S.C. 154(b) by 476 days.

(21) Appl. No.: 14/683,973

(22) Filed: Apr. 10, 2015

(65) Prior Publication Data

US 2016/0117458 A1    Apr. 28, 2016

Related U.S. Application Data

(63) Continuation-in-part of application No. 14/524,372, filed on Oct. 27, 2014, now Pat. No. 9,329,816.

(51) Int. Cl.
*G06F 3/12* (2006.01)
*G06F 19/00* (2011.01)
*G06K 15/00* (2006.01)

(52) U.S. Cl.
CPC ........ *G06F 19/3406* (2013.01); *G06F 19/323* (2013.01); *G06F 19/327* (2013.01)

(58) Field of Classification Search
CPC ....... H04L 67/16; H04L 63/10; H04L 67/025; G06F 3/1222; G06F 3/1224;

(Continued)

(56) References Cited

U.S. PATENT DOCUMENTS 6,529,164 B1 *  3/2003  Carter ................. G01S 5/0036
                                                          342/385
8,280,682 B2   10/2012  Vock et al.

(Continued)

FOREIGN PATENT DOCUMENTS

WO    20090026238 A2    2/2009
WO    20140163996 A1    10/2014

OTHER PUBLICATIONS

International Search Report and Written Opinion for Application No. PCT/US14/62444 dated Mar. 24, 2015.

(Continued)

*Primary Examiner* — Gabriel Garcia

(57) ABSTRACT

A method, apparatus, system, and computer program product are disclosed to track beacons utilizing a device management infrastructure. The method includes registering, by a device management server, at least a first detection device associated with a first location and a second detection device associated with a second location with a device management infrastructure, receiving a beacon identifier associated with a beacon detected by the first detection device, storing a first time stamp associated with detection of the beacon by the first detection device, receiving the beacon identifier associated with the beacon as detected by the second detection device, determining, based on the first time stamp and a second time stamp associated with detection of the beacon by the second detection device, an elapsed time between detection of the beacon by the first detection device and detection of the beacon by the second detection device, and reporting the elapsed time to a healthcare information system.

18 Claims, 23 Drawing Sheets

(58) Field of Classification Search
CPC .... G06F 3/1236; G06F 3/1238; G06F 3/1245;
G06F 3/1285; G06F 3/1287; G06F
3/1293; G06F 9/323; G06F 9/327; G06F
9/3406; G06K 15/1805; H04N 1/00;
H04N 1/00244; H04N 1/32106; H04N
1/44; H04N 1/4433
USPC .................................................. 358/1.1–1.18
See application file for complete search history.

(56) References Cited

U.S. PATENT DOCUMENTS

| | | |
|---|---|---|
| 2007/0093243 A1 | 4/2007 | Kapadekar et al. |
| 2008/0130042 A1 | 6/2008 | Iizuka et al. |
| 2009/0140043 A1* | 6/2009 | Graves .................. G06F 19/327 |
| | | 235/380 |
| 2010/0182640 A1 | 7/2010 | Daigo |
| 2011/0074587 A1 | 3/2011 | Hamm et al. |
| 2011/0122439 A1 | 5/2011 | Sato et al. |
| 2012/0036552 A1 | 2/2012 | Dare et al. |
| 2012/0078388 A1 | 3/2012 | Collins et al. |
| 2013/0247166 A1 | 9/2013 | Freedman et al. |
| 2014/0253941 A1 | 9/2014 | Selvaraj et al. |
| 2016/0012196 A1* | 1/2016 | Mark ..................... G06Q 10/00 |
| | | 705/2 |
| 2016/0210429 A1* | 7/2016 | Ortiz ................... G06F 19/3406 |
| 2017/0064498 A1* | 3/2017 | Manges ................. H04W 4/02 |
| 2017/0120978 A1* | 5/2017 | Shin ......................... B62H 5/20 |

OTHER PUBLICATIONS

"RFID for What? 101 Innovative Ways to Use RFID," RFID Journal, Aug. 1, 2011. Copy not provided; available in U.S. Appl. No. 14/524,372, to which priority is claimed.
International Search Report and Written Opinion for Application No. PCT/US14/62444 dated Mar. 24, 2015. Copy not provided; available in U.S. Appl. No. 14/524,372, to which priority is claimed.
Office Action for U.S. Appl. No. 14/524,372 dated Jun. 24, 2015.
International Search Report and Written Opinion for corresponding International Patent Application No. PCT/US2016/025121 dated Aug. 2, 2016.

* cited by examiner

FIG. 9

| ZATAR 🔍 Search | | | printer_demo@zebra.com 👤 |
|---|---|---|---|
| printer_demo OWNER | ⌄ | | |
| | | | ⚙ |
| ◉ Device ADD + | ⌄ | DEVICES ☰ | HOTSPOT QLN 320 |
| DEVICE GROUPS (2) | ⌄ | Name \| Location \| Status | FIRMWARE V58.19.4Z ✓ |
| W. Jackson | | ◈ 1 QLN320 | MAC ADDRESS 00:22:58:2C:54:AE |
| G1 | | Z Hotspot Gateway ZEBRA TECHNOLOGIES EDGEBOX | IP ADDRESS 0.0.0.0 |
| DEVICE PROFILES (9) | ⌄ | ◈ HotSpot QLN 320 ZEBRA TECHNOLOGIES QLN320 | SUBNET MASK 255.255.255.0 |
| 110X14 | | ◈ QLN Barca- 1 QLN320 ◉ | LOCATION MOBILE |
| Marco | | ◈ QLN320 Barca- 2 ZEBRA TECHNOLOGIES O... ◉ | MANUFACTURE/ BRAND ZEBRA TECHNOLOGIES |
| 👤 Members INVITE + | ⌄ | ◈ Rhode Island Prototype ZEBRA TECHNOLOGIES QLN320 | TYPE PRINTER |
| MEMBER GROUPS (0) | | ◈ ZD500R ZEBRA TECHNOLOGIES ZD500R | STATUS OFFLINE |
| No Member Groups | | ◈ 110X14- 820 W. Jack... ZEBRA TECHNOLOGIES 11... ◉ | DEVICES PROFILE ⌄ |
| | | □ iPad Mini APPLE IPAD | COMMANDS |
| | | | ⊙ SEND TEST PRINT |
| | | | ⊙ PRINT CONFIG LABEL |
| | | | ⊙ PRINT NETWORK SETTINGS |
| | | | ⊙ FEED ONE LABEL |
| | | | ⊙ REBOOT |
| | | | ⊙ SEND 2PL COMMAND |
| | | | ⊙ CALIBRATE MEDIA |
| | | | ⊙ RESET TO FACTORY DEFAULT |

FIG. 12

METHOD AND APPARATUS FOR MANAGING REMOTE DEVICES AND ACCESSING REMOTE DEVICE INFORMATION

CROSS REFERENCE TO RELATED APPLICATIONS

This application is a continuation-in-part of U.S. patent application Ser. No. 14/524,372, filed Oct. 27, 2014, the entire contents of which are incorporated herein by reference.

TECHNOLOGICAL FIELD

Example embodiments of the present invention relate generally to systems that provide information between devices and software applications and, more particularly, to systems and related embodiments, which are configured for managing and sharing access to data among a plurality of disparate devices.

BACKGROUND

Applicant has discovered problems with current methods for providing information to and from devices. Through applied effort, ingenuity, and innovation, Applicant has solved many of these identified problems by developing a solution that is embodied by the present invention, which is described in detail below.

BRIEF SUMMARY

Accordingly, methods, apparatuses, and computer program products are provided for providing information to and from devices. Example embodiments may include a method for managing access to a plurality of devices. The method may include receiving a first set of device permissions for a first particular device of the plurality of devices, the set of device permissions received from a first user account, the first user account being authorized to manage the first particular device, and receiving a second set of device permissions for a second particular device of the plurality of devices. The set of device permissions received from a second user account different from the first user account. The second user account may be authorized to manage the second particular device and being unauthorized to manage the first particular device. The method may also include receiving a first set of device information from the first particular device, receiving a second set of device information from the second particular device, providing the first set of device information based on the first set of device permissions, and providing the second set of device information based on the second set of device permissions. The first set of device information may be provided based on contents of the first set of device information. The first set of device information may be presented in a JavaScript Object Notation format. The first set of device information may be provided via a Representational State Transfer API. The first set of device information may be provided to at least one of an application, a device, or a user portal. The first particular device may be a printer.

Embodiments may also include a system for providing a device management infrastructure. The system may include a plurality of devices configured to provide device information to a device management server, and a remote server comprising the device management server. The device management server may be configured to receive the device information, to provide the device information based on one or more permission settings for the plurality of devices, and to provide a device management interface. The device management interface may include an interface for modifying the permission settings for one or more particular devices associated with a user account accessing the device management interface. The device management server may be further configured to process the device information to determine the contents of the device information, and wherein the device information is provided based on the contents of the device information. The device information may be provided at least in part based on the contents of the device information by assigning a device that provided the device information to a particular device group based on the contents of the device information. The device management server may be further configured to provide a reduced portion of the device information to a receiver of the device information, and the reduced portion may be determined based on a set of permissions associated with the receiver.

Embodiments may also include method for managing access to a plurality of devices. The method may include receiving device information from at least one device, the at least one device managed by a first user account, determining, using a processor, a receiver for the device information based on one or more device groups to which the at least one device belongs, wherein the receiver comprises at least one of an application, a device, or a user account that is authorized to access a device group of the one or more device groups, wherein the receiver is managed by a second user account, and providing the device information to the determined receiver. The method may also include assigning the at least one device to a second device group based on the contents of the device information.

Embodiments may also include a method for managing access to a plurality of devices. The method may include receiving device information from at least one device, generating, using the device information, a graphical representation of a status of the at least one device, receiving, from a requesting device associated with a particular user account, an access request for the graphical representation, and in response to determining that the particular user account is authorized to access the graphical representation, providing the graphical representation to the requesting device. The graphical representation may be provided via a web portal. An update interval for the graphical representation may be determined based on one or more characteristics of the at least one device. The one or more characteristics may include at least one of a maximum bandwidth or a battery status.

Embodiments may also include a gateway device for providing device information to a device management infrastructure. The gateway device may include a memory subsystem, a communication interface for receiving device information in a device-native format and transmitting the device information to a remote server in a device-agnostic format, and a device information processor configured to convert the device information into a device-agnostic format by encoding the device information in a JavaScript Object Notation (JSON) object.

Embodiments may also include a method for managing one or more devices via a device management infrastructure. The method may include receiving device information from at least one of the one or more devices via a local area network, detecting a firewall between the local area network and a remote server implementing the device management infrastructure, circumventing the firewall to enable communications with the remote server, and transmitting the device information to the remote server.

Embodiments may also include an apparatus for managing one or more devices using a device management infrastructure. The apparatus may include a memory, and at least one processor configured to receive external device information from at least one first external device other than the apparatus, to determine internal device information for the apparatus, and to transmit the internal device information and the external device information to a remote server implementing the device management infrastructure. The apparatus may be a mobile phone. The apparatus may include a display, and the processor may be further configured to receive additional device information from the remote server, the additional device information received by the remote server from a second external device and to display the additional device information on the display. The processor may be further configured to detect the presence of the at least one first external device via a device discovery process and to request the device information from the at least one first external device in response to detecting the presence of the at least one first external device.

Embodiments may also include an apparatus. The apparatus may include first communications circuitry configured to enable the apparatus to transmit and/or receive a device information message by at least formatting the device information message in a device-native format, second communications circuitry configured to enable the apparatus to transmit and/or receive the device information message by at least formatting the device information message in a device-agnostic format, and a processor configured to determine which of the first communications circuitry or the second communications circuitry to use to transmit and/or receive the device information message. The apparatus may be a printer and the device information message comprises a printer command. The printer command may be encoded in a printer control language. The printer control language may be Zebra Programming Language.

Embodiments may also include a method for managing devices via a device management infrastructure. The method may include receiving a first set of device information in a device-native format from one or more devices in communication with a gateway device, converting the first set of device information to a device-agnostic format, and transmitting the first set of device information in the device-agnostic format to a remote server. The method may also include receiving a second set of device information in the device-agnostic format, converting the second set of device information to the device-native format, and transmitting the second set of device information in the device-native format to a device, wherein the device provided the first set of device information. The device-agnostic format may be JavaScript Object Notation and the device-native format may be Zebra Programming Language. The device may be a printer.

Embodiments include a method for tracking beacons utilizing a device management infrastructure. The method includes registering, by a device management server, at least a first detection device associated with a first location and a second detection device associated with a second location with a device management infrastructure, receiving, via the device management infrastructure and from the first detection device, a beacon identifier associated with a beacon detected by the first detection device, storing a first time stamp associated with detection of the beacon by the first detection device, receiving, via the device management infrastructure and from the second detection device, the beacon identifier associated with the beacon as detected by the second detection device, determining, based on the first time stamp and a second time stamp associated with detection of the beacon by the second detection device, an elapsed time between detection of the beacon by the first detection device and detection of the beacon by the second detection device, and reporting the elapsed time to a healthcare information system.

The beacon may include a wristband provided to a patient of a healthcare organization associated with the healthcare information system. The first location may be a hospital registration desk and the second location is a hospital treatment room. The beacon is a Bluetooth Low Energy (BLE) beacon. The first detection device and the second detection device may be tablet computers. The tablet computers may be configured to communicate with a management server via a device management infrastructure. The tablet computers may communicate with the device management infrastructure via a wireless Internet connection. The wireless Internet connection may include a publicly available wireless connection provided by a healthcare organization, a private wireless connection provided by the healthcare organization, and a cellular network. The method may also include providing the elapsed time to the second detection device for display on a display coupled to the second detection device.

Embodiments also include an apparatus for tracking beacons utilizing a device management infrastructure. The apparatus includes a device management server configured to register at least a first detection device associated with a first location and a second detection device associated with a second location with a device management infrastructure, receive, via the device management infrastructure and from the first detection device, a beacon identifier associated with a beacon detected by the first detection device, store a first time stamp associated with detection of the beacon by the first detection device, receive, via the device management infrastructure and from the second detection device, the beacon identifier associated with the beacon as detected by the second detection device, determine, based on the first time stamp and a second time stamp associated with detection of the beacon by the second detection device, an elapsed time between detection of the beacon by the first detection device and detection of the beacon by the second detection device, and report the elapsed time to a healthcare information system.

The beacon may include a wristband provided to a patient of a healthcare organization associated with the healthcare information system. The first location may be a hospital registration desk and the second location may be a hospital treatment room. The beacon may be a Bluetooth Low Energy (BLE) beacon. The first detection device and the second detection device may be tablet computers.

The tablet computers may be configured to communicate with a management server via a device management infrastructure. The tablet computers may communicate with the device management infrastructure via a wireless Internet connection. The wireless Internet connection may include a publicly available wireless connection provided by a healthcare organization, a private wireless connection provided by the healthcare organization, and a cellular network. The device management server may be further configured to provide the elapsed time to the second detection device for display on a display coupled to the second detection device.

Embodiments also include a method for tracking beacons utilizing a device management infrastructure. The method includes registering, by a detection device, with a device management infrastructure via a wireless Internet connection, detecting a presence of a beacon via a Bluetooth Low Energy (BLE) protocol, determining an identifier associated with the beacon, and reporting, via the device management infrastructure, the detected presence of the beacon.

The method may also include displaying the detected presence of the beacon on a display coupled to the detection device. The method may also include displaying, on the display coupled to the detection device, an elapsed time associated with the presence of the beacon.

Embodiments also include a detection device for tracking beacons utilizing a device management infrastructure. The detection device is configured to register with a device management infrastructure via a wireless Internet connection, detect a presence of a beacon via a Bluetooth Low Energy (BLE) protocol, determine an identifier associated with the beacon, and report, via the device management infrastructure, the detected presence of the beacon.

The detection device may also include a display. The detection device may be further configured to display the detected presence of the beacon on the display. The detection device may be further configured to display, on the display, an elapsed time associated with the presence of the beacon.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Figure 1:
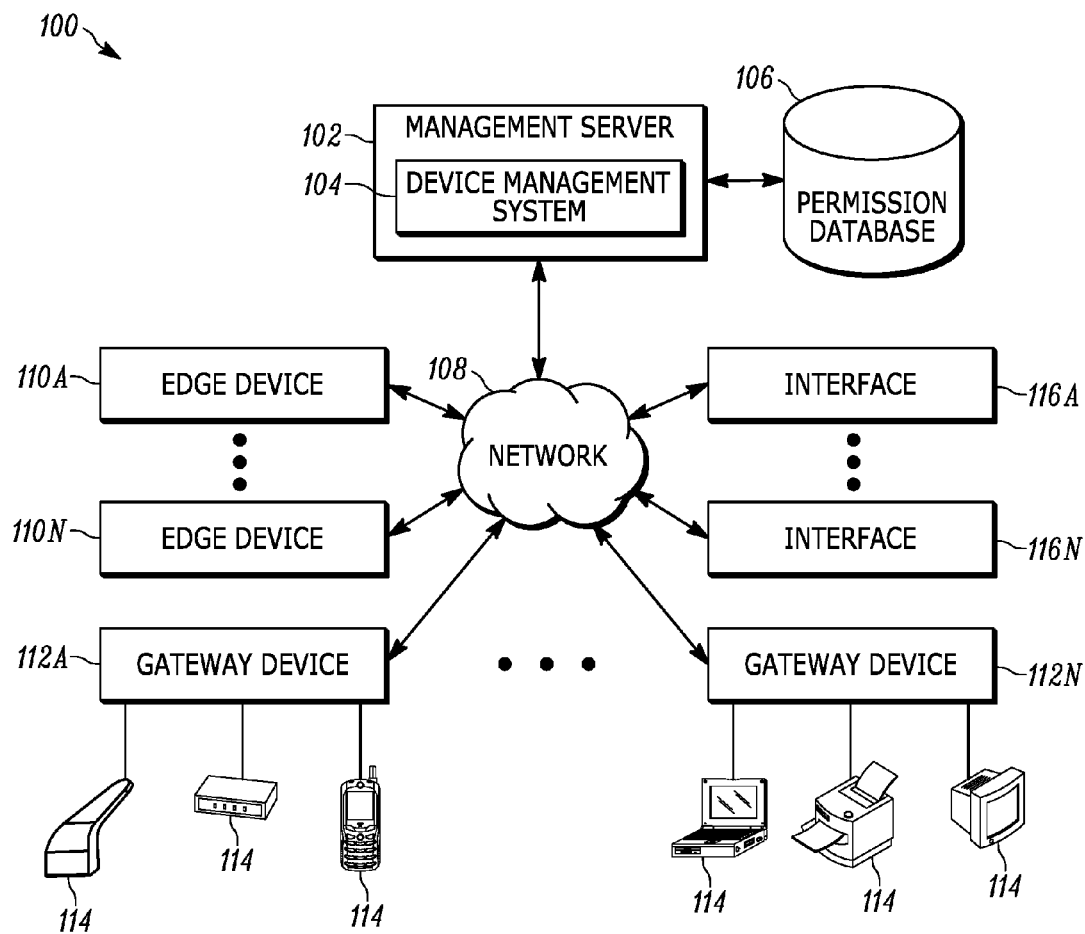
Figure 2A:
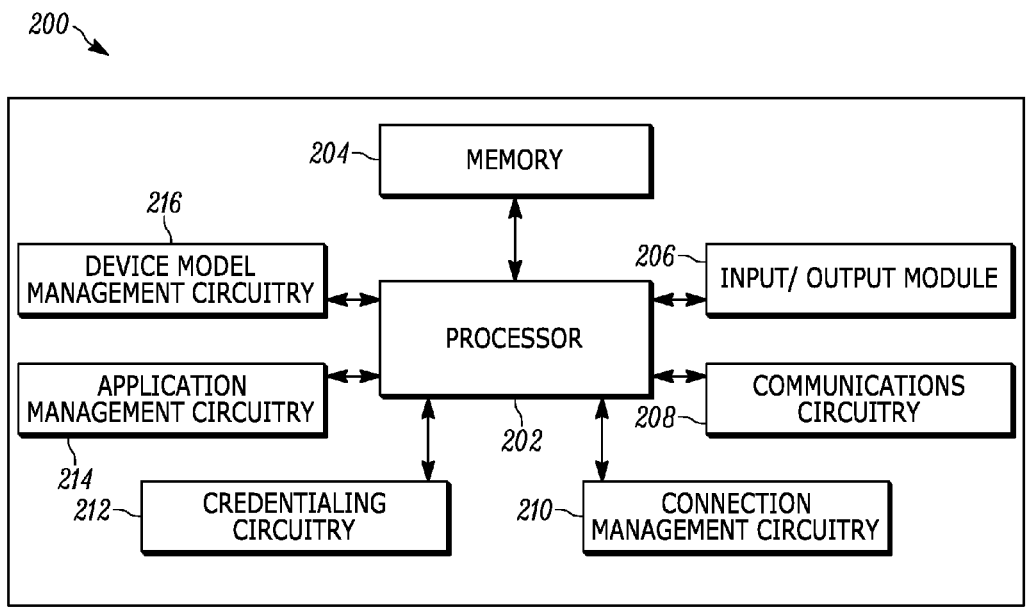
Figure 2B:
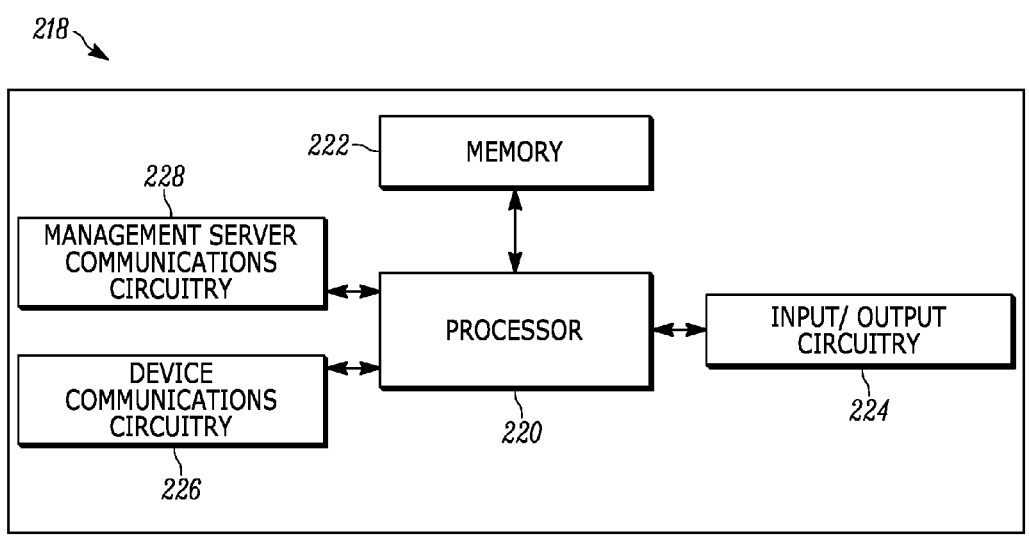
Figure 3:
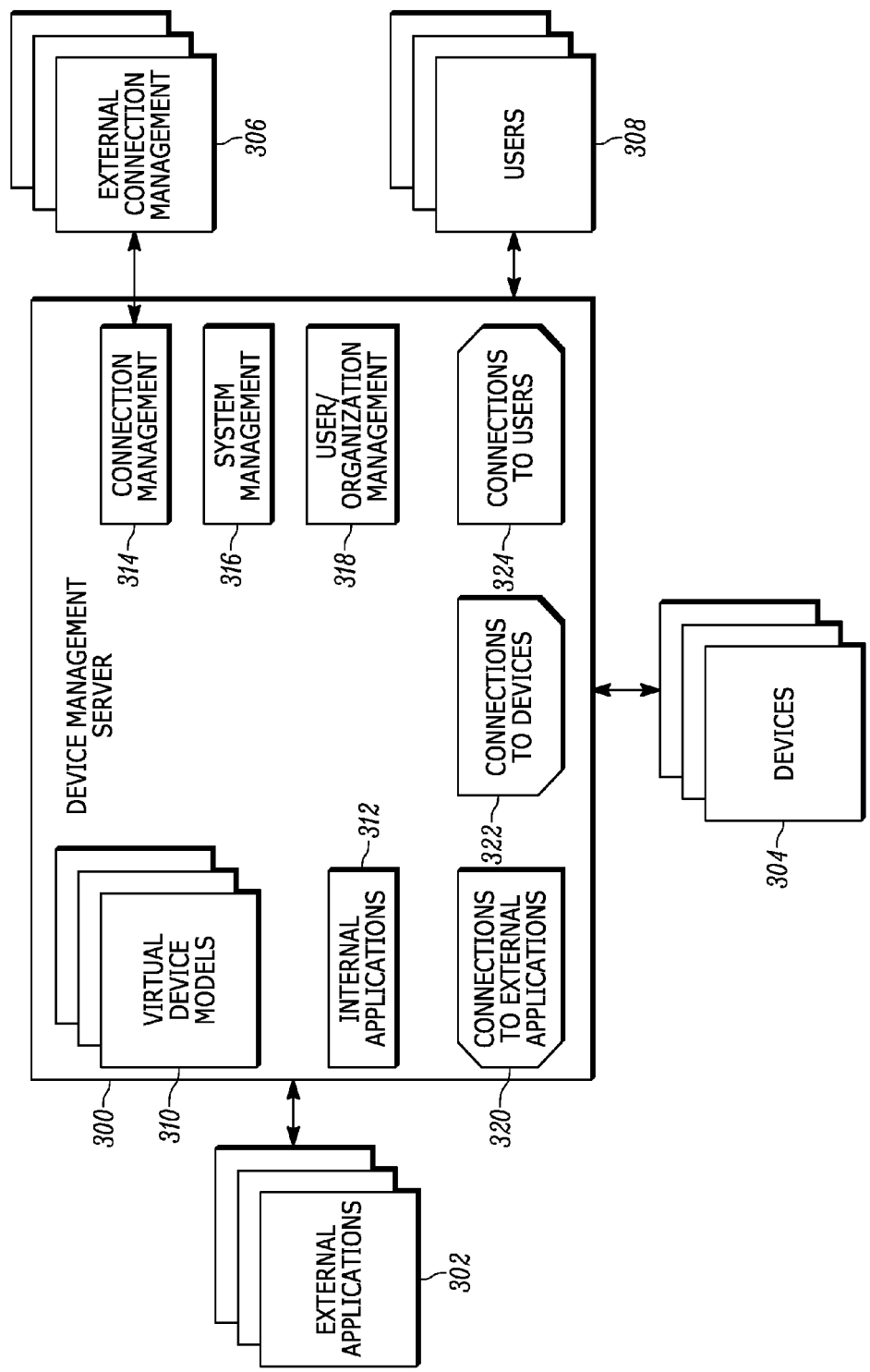
Figure 4:
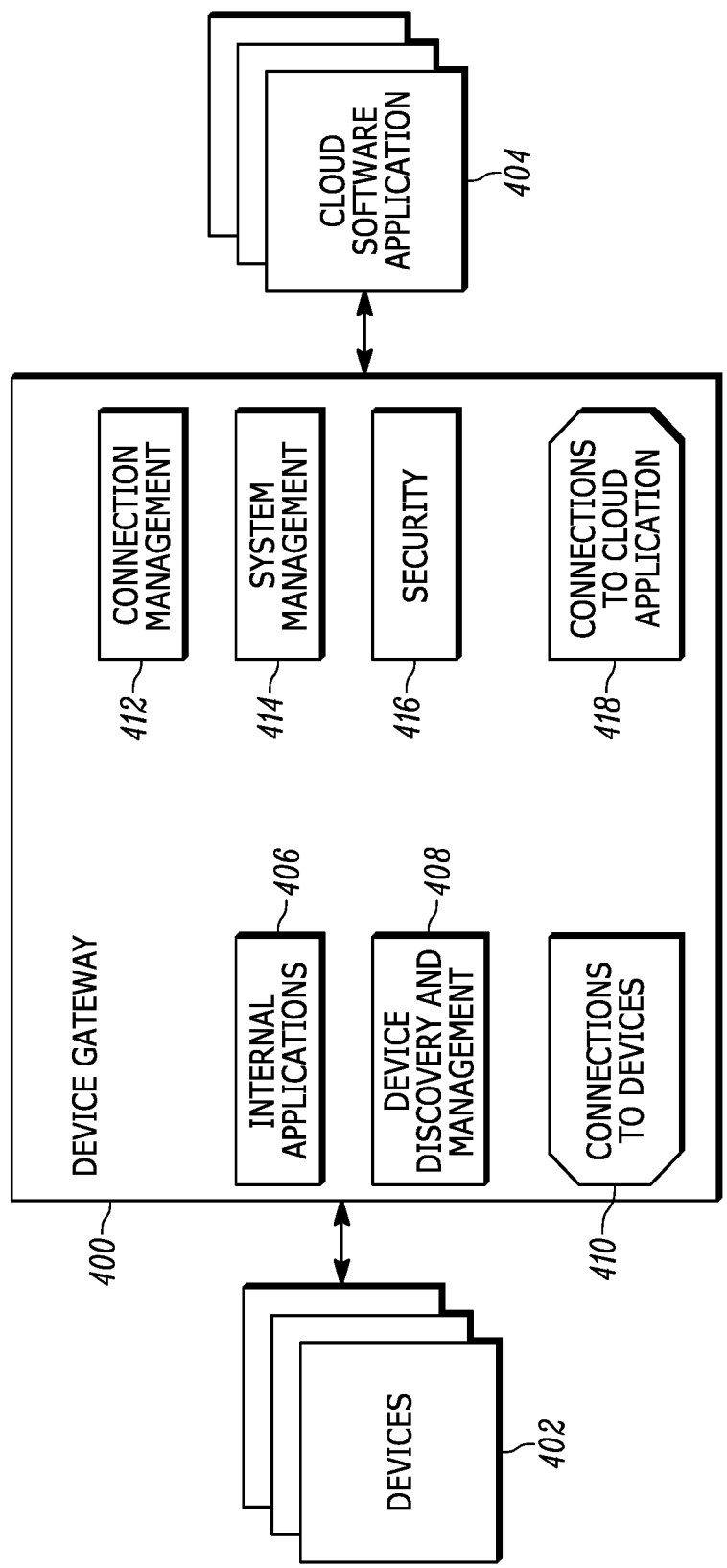
Figure 5:
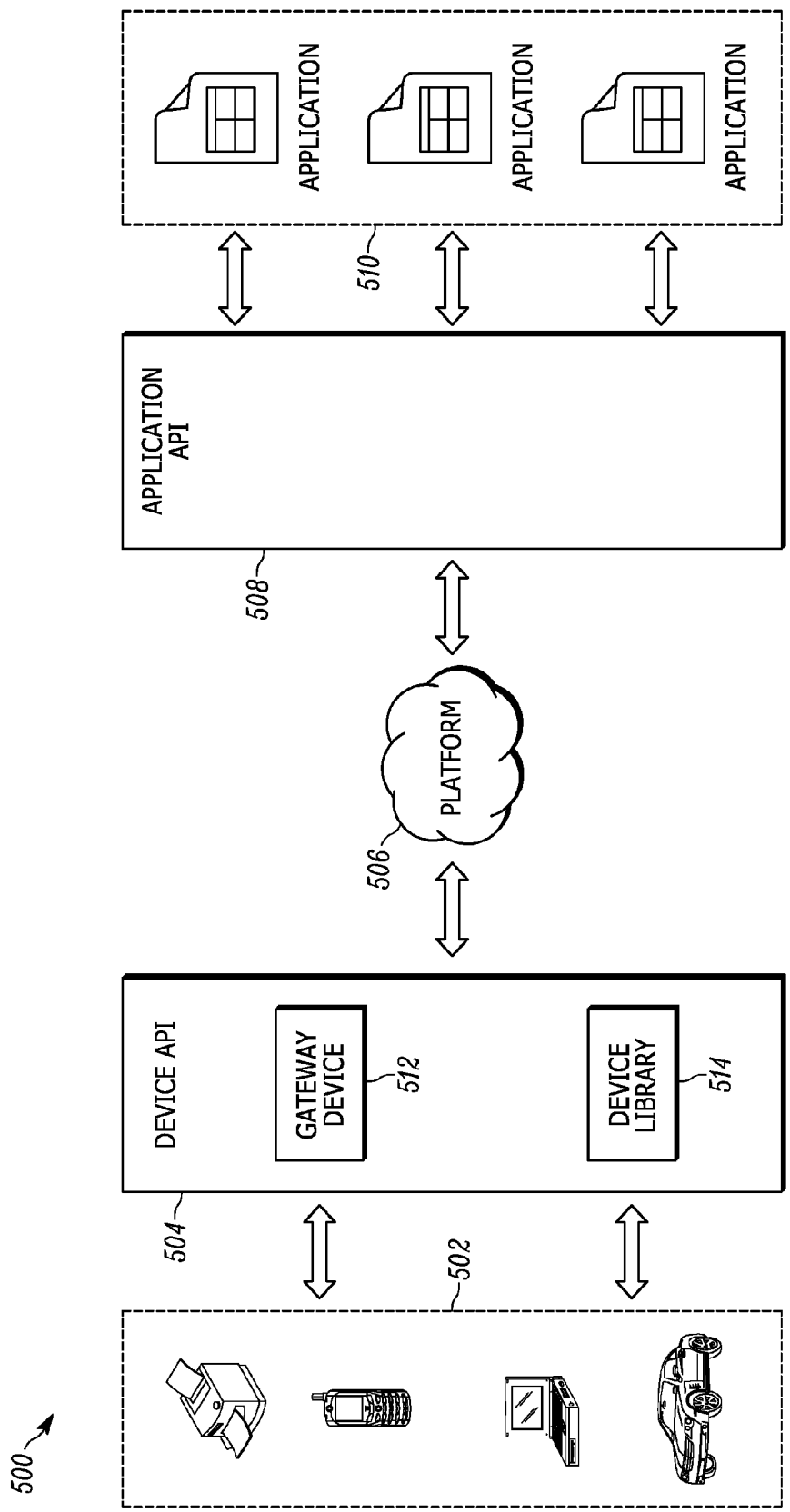
Figure 6:
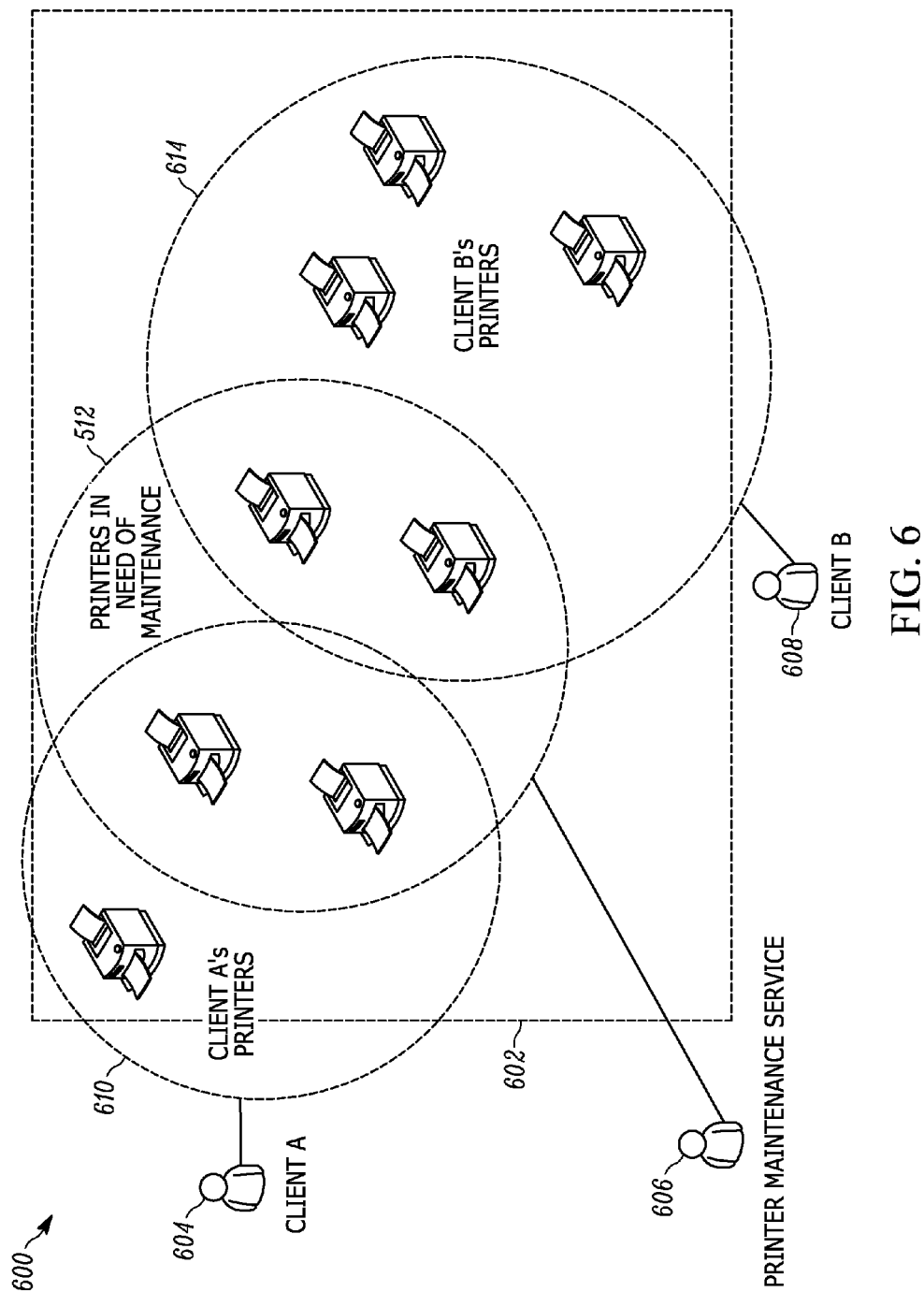
Figure 8:
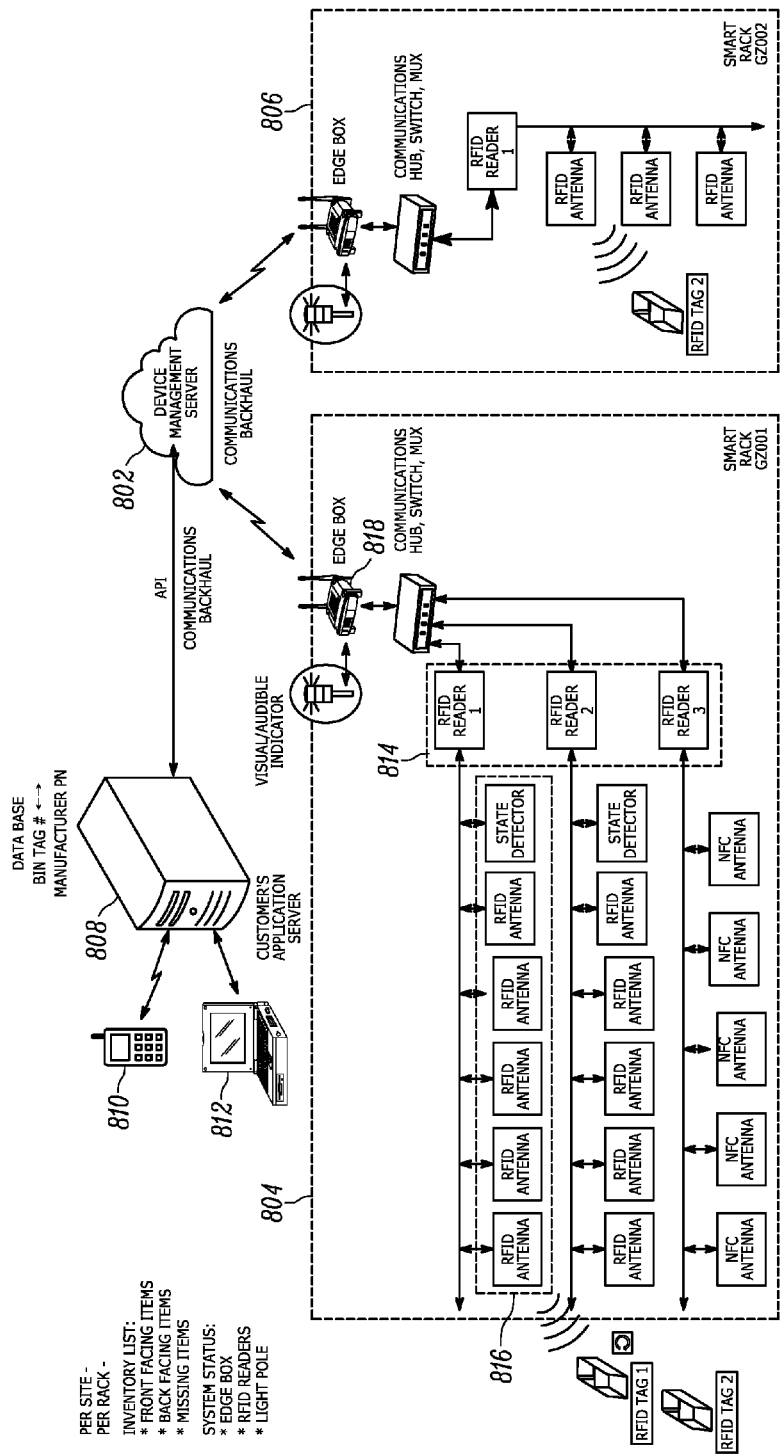
Figure 15:
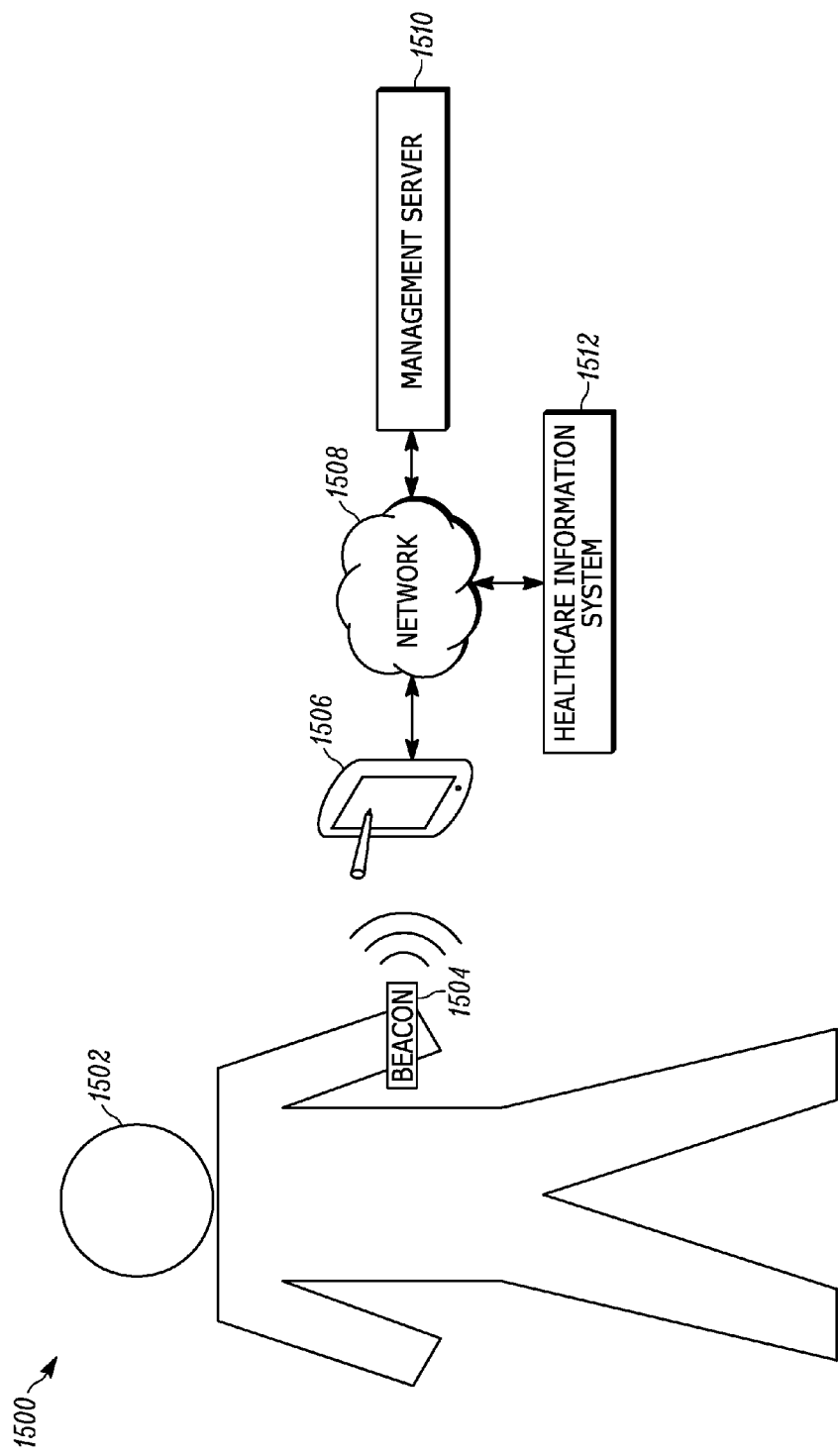
Figure 16:
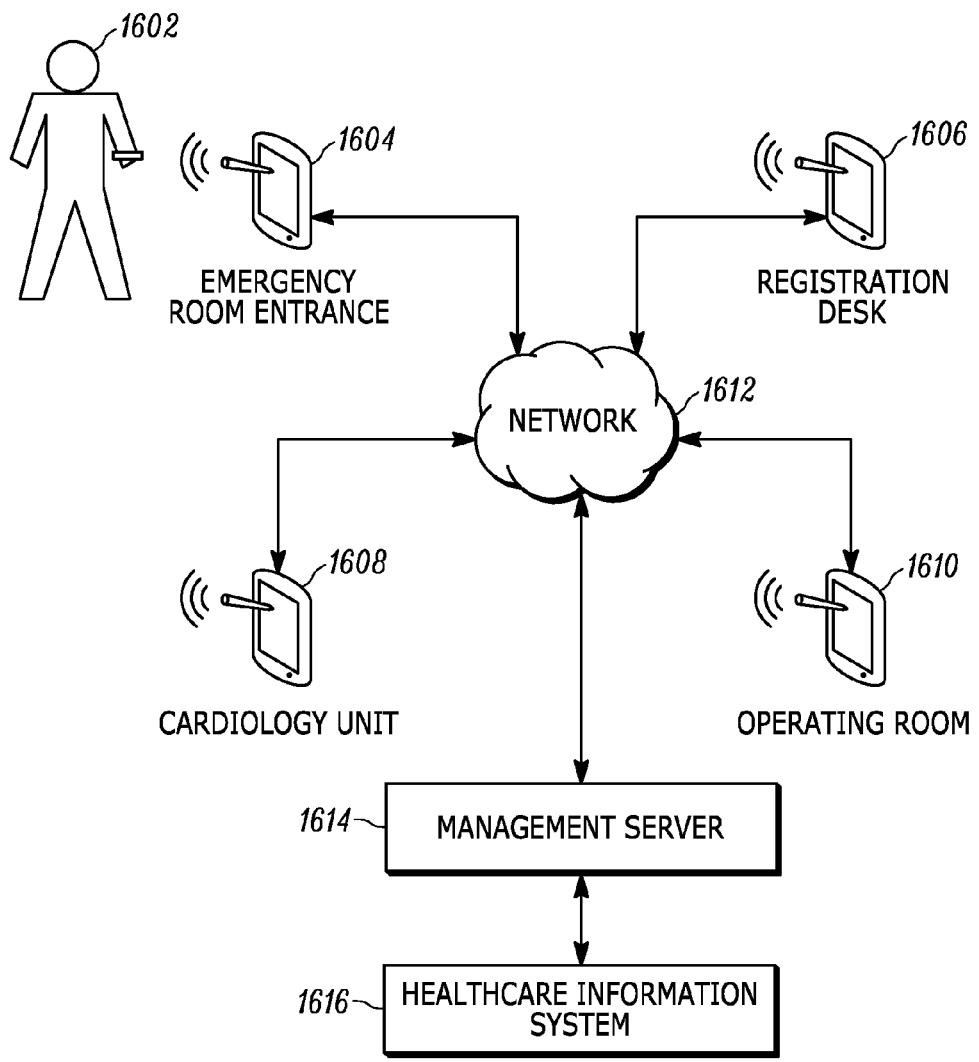
Figure 17:
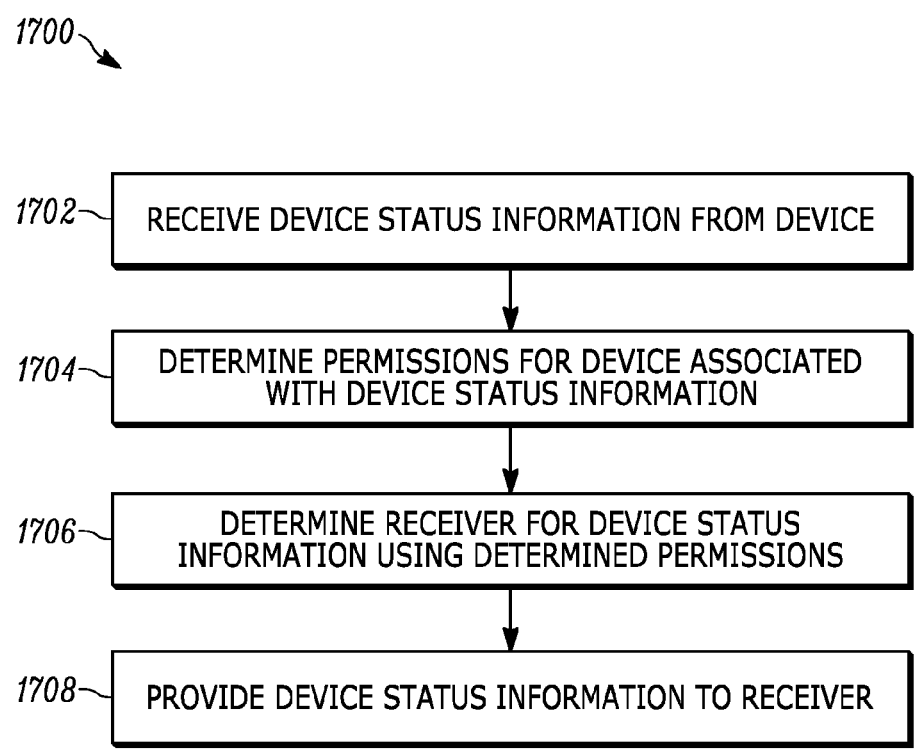
Figure 18:
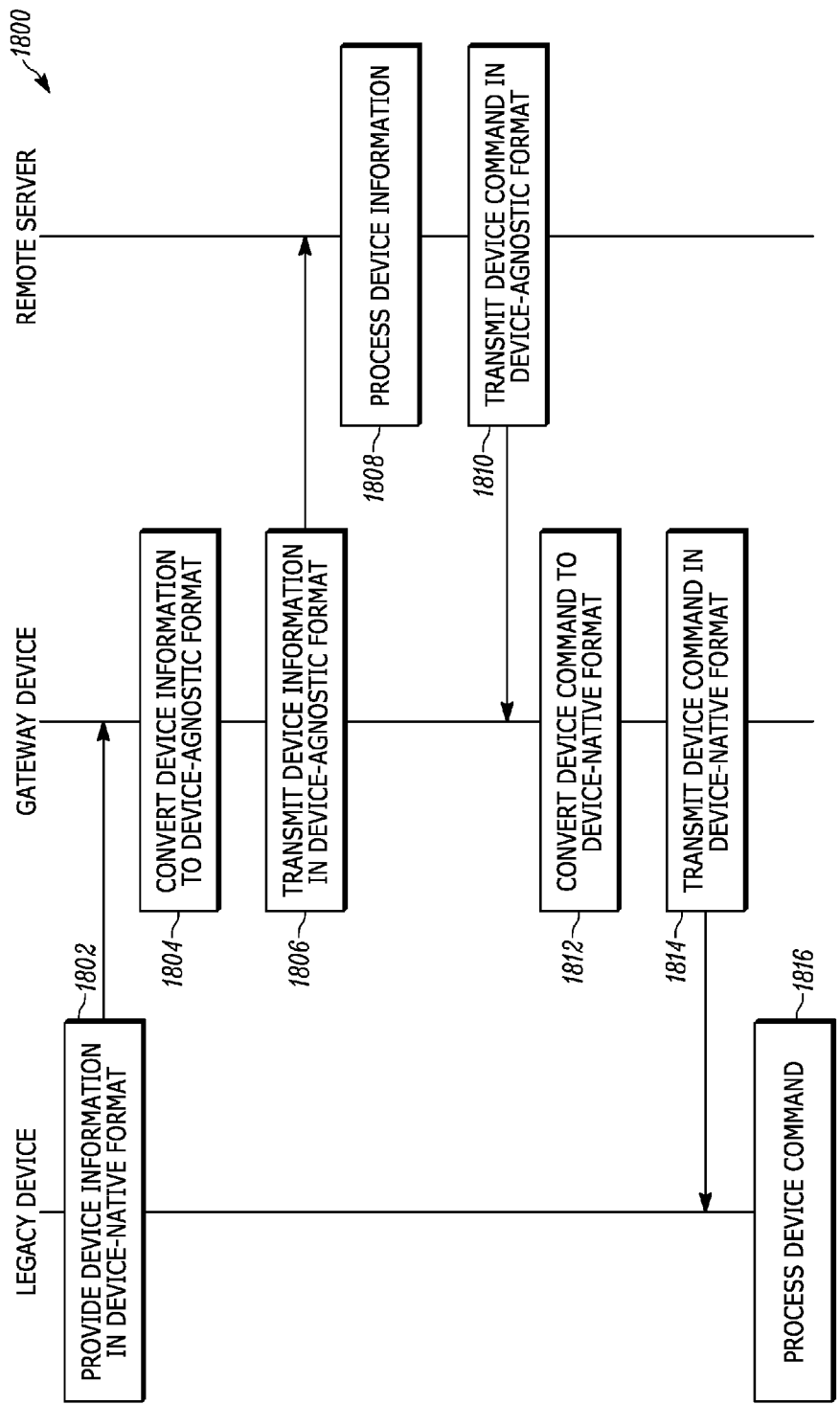
Figure 19:
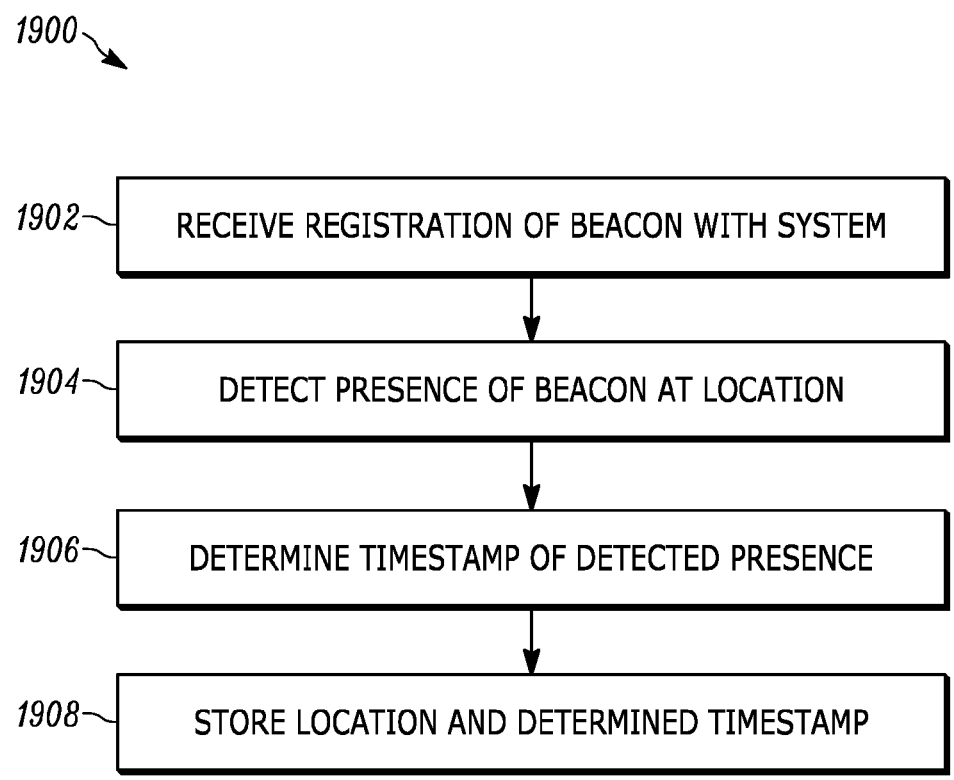
Figure 20:
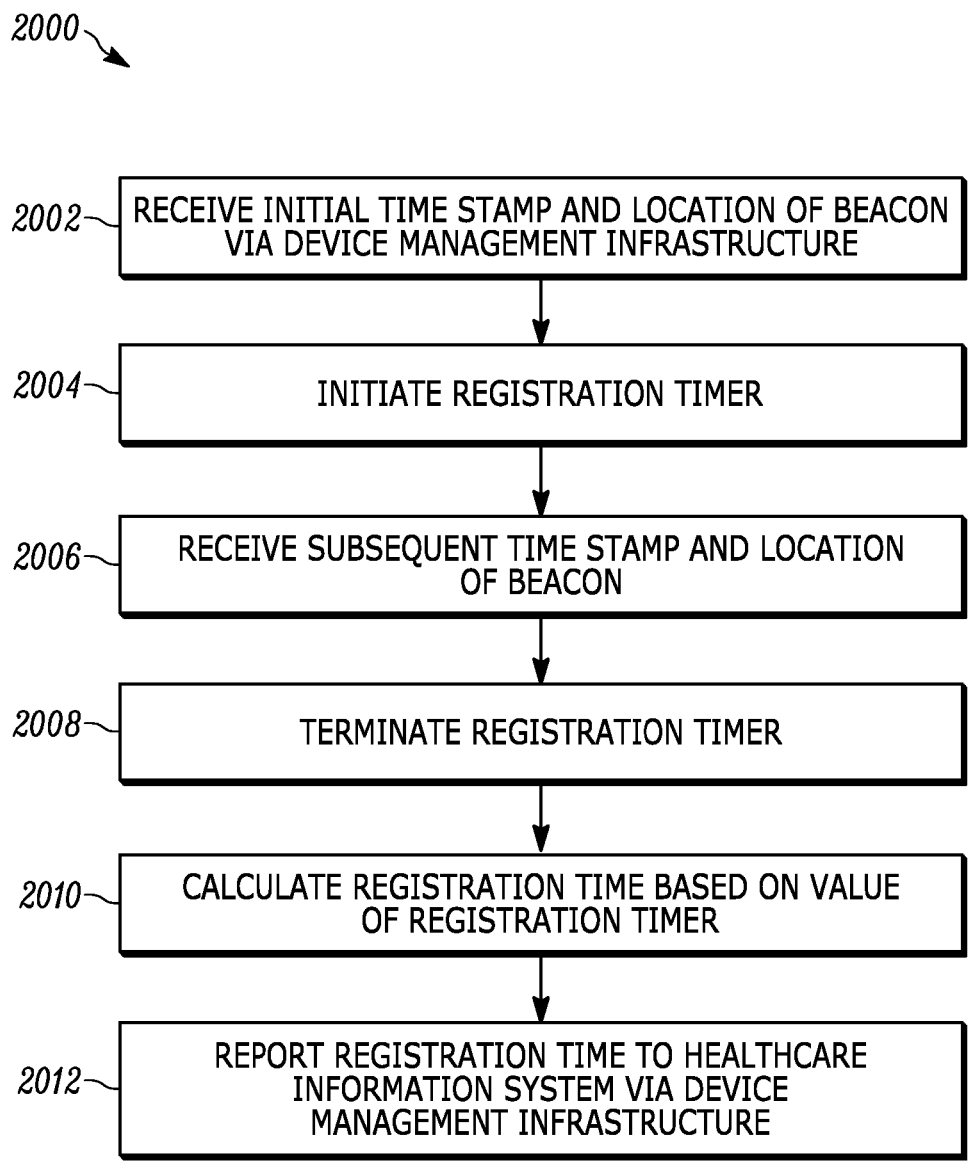

Having thus described certain example embodiments of the present disclosure in general terms, reference will now be made to the accompanying drawings, which are not necessarily drawn to scale, and wherein:

FIG. 1 illustrates an example system within which embodiments of the present invention may operate;

FIG. 2A illustrates a block diagram showing an example device for use in a device management system, in accordance with some embodiments of the present invention;

FIG. 2B illustrates a block diagram showing an example device gateway for use in a device management system, in accordance with some embodiments of the present invention;

FIG. 3 illustrates a block diagram of a data flow to and from an example device management server and components thereof, in accordance with some embodiments of the present invention;

FIG. 4 illustrates a block diagram of a data flow to and from an example device gateway in accordance with some embodiments of the present invention;

FIG. 5 illustrates a block diagram of communication among devices and applications utilizing a device management platform in accordance with some embodiments of the present invention;

FIG. 6 illustrates a device grouping in accordance with some embodiments of the present invention;

FIGS. 7A-7D illustrate an example multi-tenant device management infrastructure in accordance with example embodiments of the present invention;

FIG. 8 illustrates an example inventory system for use in accordance with some embodiments of the present invention;

FIGS. 9-14 illustrate example interfaces for managing devices in accordance with some embodiments of the present invention;

FIG. 15 illustrates a block diagram of an example embodiment utilizing a device management infrastructure in association with healthcare information systems in accordance with some embodiments of the present invention;

FIG. 16 illustrates a system diagram of a device management infrastructure in communication with healthcare information systems in accordance with some embodiments of the present invention;

FIG. 17 illustrates a flow diagram of an example method for managing device information in accordance with some embodiments of the present invention;

FIG. 18 illustrates a signal diagram of an example method for establishing communications between a legacy device and a device management infrastructure via a gateway device in accordance with some embodiments of the present invention;

FIG. 19 illustrates a flow diagram of an example method for utilizing a device management infrastructure for beacon tracking and time stamp capturing in accordance with some embodiments of the present invention; and FIG. 20 illustrates a flow diagram of an example method for tracking registration times in a healthcare setting using a device management infrastructure in communication with a healthcare information system in accordance with some embodiments of the present invention.

DETAILED DESCRIPTION

Some embodiments of the present invention will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Overview and Definitions

Businesses typically use various software applications such as Enterprise Resource Planning (ERP) systems, Remote Device Management (RDM) systems, Mobile Device Management (MDM) systems, Warehouse Management Systems, Energy Management Systems or Fleet Logistics Systems. Healthcare facilities may have patient management systems. Retail stores, entertainment and recreation venues have applications that manage customer interactions. All of these systems rely on data from the physical world. Increasingly the data from the physical world is supplied by devices that identify objects, sense conditions and track locations of objects. These applications also frequently must actuate devices to affect real world objects, such as printing a label, sorting items on a conveyor, changing a temperature or rerouting a vehicle. The overall benefits that businesses derive from these applications are frequently proportional to the number of devices that provide or receive data to or from the applications. However, as the number of devices in communication with the system increases, so too does the complexity of implementing communications between and among these disparate devices. Furthermore, many organizations utilize software applications that are remotely hosted in cloud based data centers. This makes connectivity to devices that gather physical world data even more difficult. Additionally, discovery and configuration of both wireless and wired devices to enable communication via a device management infrastructure introduces new challenges, such as the need to traverse an organization's firewall. As the costs of Internet connected devices continue to decrease, organizations are likely to employ increasing numbers of network-aware sensing devices. This substantial increase in the number of connected devices creates a significant technical hurdle in connecting to and managing the devices.

Furthermore, the inventors have identified that even when connectivity is established to devices, obtaining, organizing, managing, processing, and providing data received to those devices in a coherent, robust manner is difficult. Existing frameworks fail to provide technical solutions for managing access permissions for devices, providing credentialing mechanisms to access data received from those devices, and the like. To address these problems, the inventors have created a platform that addresses these technical problems, providing for increased availability of data, improved network bandwidth due to management of which connections receive which data, and the like.

In view of these technical problems and others that may arise from time to time, some organizations may be not be able to take advantage of the cost savings, efficiency increases, and performance improvements offered by these software applications that utilize data from the physical world. Furthermore, even organizations that have connectivity between software applications and devices are limited by multiple proprietary system configurations and communication protocols. Accordingly, to overcome these problems, example embodiments of the present invention provide a robust, flexible, and configurable platform that provides systems and methods that combine software applications with devices without the need for users to purchase, lease, or maintain their own server hardware. Embodiments provide a robust platform and architecture that enables multiple users and organization to leverage the capabilities of a system using device information while reducing or eliminating the overhead costs associated with such a system. Embodiments further provide the capability to manage and share access to data among a plurality of heterogeneous devices. Embodiments provide for managing device access levels such that access to device state may be provided to other devices, applications, and users via a unified platform, and architecture. Embodiments may facilitate these services and benefits through a cloud-based service architecture that allows for the sharing of data among devices while preserving user security settings and access rights based on permissions established by the users. Embodiments may also be operable to provide device information to devices, applications, and the like external to the architecture, such as by exposing such state information via an Application Programming Interface (API).

In particular, the inventors have recognized that embodiments may have particular applicability in a healthcare context to facilitate the locating and tracking of patients within a healthcare system. Embodiments may also be employed to determine the particular time at which a patient enters a particular location within the healthcare system for the purpose of determining analytics related to registration times, the length of time between arrival at the healthcare system and the start of treatment, and the like. Embodiments may leverage the ability of a variety of devices to communicate via the device management infrastructure to reduce costs and provide access to data in a flexible, robust way that meets applicable privacy standards. Embodiments may implement such benefits through the use of a system that limits access to information that personally identifies patients by only passing location information and beacon reference information into a healthcare information system, such that no patient information is exposed to elements of the system involved in location tracking or shared via the device management infrastructure.

Embodiments may leverage devices placed about a healthcare organization (HCO) at particular locations for the purpose of patient tracking and measurement of registration metrics. These devices may also provide real-time feedback, such as by displaying patient identifiers, locations, simple messages, and the like as determined based on patient tracking process and based on analytic data.

Embodiments also advantageously provide for patient tracking services in rooms that are shielded or otherwise subject to electromagnetic interference, such as catheterization rooms. For example, detection devices in shielded rooms may communicate with wireless access points located within the same shielded room, and those access points may be connected to a network via a wired connection to avoid electromagnetic interference caused by the shielding. The inventors have also conducted extensive study and analysis to identify particular signal output settings for beacons and detection settings for detection devices. For example, the inventors have determined that, in some embodiments, stronger output signals and higher broadcast frequency from the beacons, coupled with filtering of detected signals on detection devices may be preferable over weaker output signals without filtering on detection devices.

The inventors have also determined that different room geographies and detection scenarios may require different detection settings. In particular, the inventors have identified particular detection settings that may be employed as a template or starting point for particular room configurations. For example, building entrances, straight corridors, corridors with corners, and shielded rooms (e.g., catheterization rooms) may require different settings.

As a particular example, in a building entrance, opening doors may assist with obtaining a strong signal when a patient wearing a beacon enters the building. However, such entrances are often unpredictable with large amounts of coming and going traffic, doors being held open, and the like, such that a high detection device sensitivity and fast scanning rate are preferable to ensure proper beacon detection by the detection device. Such tablets may employ a "capture threshold" for a capture signal above which a beacon is identified as present, and a "release threshold" below which the beacon is identified as no longer present. In some embodiments, detection devices may be stored or housed within ruggedized metal casings. Such casings may block the signal from beacons and thus require more sensitive capture settings by the detection device. Depending upon the particular entrance, different entrances may also use different capture settings. For example, at a first entrance an incoming patient may pass directly in front of a detection device, while in another entrance the patient may approach the device but then turn left or right prior to passing directly in front of the detection device. In such cases, the first entrance may be configured with a detection device with a lower sensitivity (e.g., a higher capture threshold) than the other entrance. As a result, in entrances the detection frequency may be set to once every 200 ms, a capture threshold (e.g., a number of decibels per meter) may be set at 85 or 80 dB/m (accounting for different entrance geography as described above, and a release threshold of 95 or 90 dB/m.

Alternatively, in scenarios where the detection device is located within a straight corridor, the detection device may be configured to detect the beacon for scenarios where patients quickly pass by the detection device. Accordingly, detection settings with a high degree of sensitivity may be employed, though such scenarios may typically be less sensitive than detection devices positioned at entrances. As with the detection devices at the entrance, the corridor detection devices may be housed within a ruggedized metal casing, requiring more sensitive capture settings to be employed to account for signal attenuation caused by the casing. To ensure that an event of the beacon leaving the area is properly detected, the release threshold may be set at greater than or equal to 95 dB/m. As with the entrance detection device, the detection frequency may be set to once every 200 ms. The capture threshold may be set to 80 dB/m.

For detection devices positioned within a corridor with a corner, there may be more time to capture the presence of the beacon due to the need for the patient to traverse the corner. Corners may also assist with signal detection and differentiation between nearby signals and signals that are farther away. Accordingly, capture thresholds and release thresholds may be set to higher values, and a lower difference between the capture threshold and release threshold may be employed. As such, detection devices in corner locations may be considered more accurate than some other detection devices. The detection frequency may be set to once every 250 ms, the capture threshold may be 80 dB/m, and the release threshold may be 86 dB/m.

For detection devices positioned in particular rooms such as catheterization rooms, a slower beacon detection frequency may be used, since patients may typically stay in such rooms for a longer period of time. To reduce the chance of "flickering" (a scenario where minor signal fluctuations cause the beacon to appear to be present and missing over a short period of time), a 20 dB/m difference between capture and release thresholds may be employed. Since such rooms may be shielded by the walls and closed doors, a lower capture threshold may be employed to avoid detecting beacons passing by the door to the room. Since such rooms are less likely to be high traffic areas, the detection device may not include a ruggedized metal casing. In such cases, the detection frequency may be set to once every 300 ms, with a capture threshold of 75 dB/m and a release threshold of 90 dB/m.

Although some specific examples of detection settings have been given above, it should be appreciated that different scenarios may employ different detection settings based on the particular detection device hardware used, the particular beacon hardware used, the particular room/corridor geography, and various other factors.

Embodiments of detection devices for tracking patient locations may include a capability to communicate via a variety of different wireless protocols, such as Wi-Fi, LTE, and/or the like. In some embodiments, the ability to communicate via multiple different protocols enhances the ability of the detection device to provide data to a device management infrastructure, increasing the flexibility in where and how that detection device may be used.

Embodiments may also include particular beacon devices for patient tracking. In some embodiments, the beacon device is affixed to a wrist bracelet with a "slap" design, such as a design that incorporates one or more layers of flexible bistable spring bands that are capable of being stored in a straightened position, but which curve about the user's wrist to secure the band to the wrist when applied to the wrist.

As used herein, the terms "data," "content," "information," and similar terms may be used interchangeably to refer to data capable of being transmitted, received, proxied, and/or stored in accordance with embodiments of the present invention. Thus, use of any such terms should not be taken to limit the spirit and scope of embodiments of the present invention. Further, where a computing device is described herein to receive data from another computing device, it will be appreciated that the data may be received directly from the another computing device or may be received indirectly via one or more intermediary computing devices, such as, for example, one or more servers, relays, routers, network access points, base stations, hosts, and/or the like, sometimes referred to herein as a "network." Similarly, where a computing device is described herein to send data to another computing device, it will be appreciated that the data may be sent directly to the another computing device or may be sent indirectly via one or more intermediary computing devices, such as, for example, one or more servers, relays, routers, network access points, base stations, hosts, and/or the like.

As used herein, the term "device management infrastructure" should be understood to refer to a system configured to provide a plurality of users with access to device information from one or more devices configured to communicate with one or more remote servers. The device management infrastructure may be configured to manage access of particular devices by the users. The device management infrastructure may allow users to determine which users, devices, and/or applications are able to receive device information for devices managed by the particular user. For example, a user may use the device management infrastructure to configure a particular device (e.g., a printer owned by a particular client) to communicate with an application managed by another user (e.g., a printer maintenance application operated by a printer maintenance service). The communication between the device and application may be facilitated by the device management infrastructure. To this end, the device management infrastructure may act as a proxy for transferring device information to, from, and among various devices in communication via the device management infrastructure. The device management infrastructure may facilitate these proxy operations by enabling communication of device information in a device-agnostic format.

In some embodiments, the device management infrastructure may be configured to authenticate user credentials for a user account. User accounts may be associated with particular sets of access rights for various devices and applications. For example, a user account may "own" several devices, thereby having complete or full access rights to device information and to set permissions for each owned device, while having more limited access rights to certain devices owned by other users. In some embodiments, a user may configure certain devices to report certain data to other devices, users, or applications. For example, the user may expose selected device information to one user (e.g., a "ribbon out" printer status may be exposed to a printer maintenance service), but may not expose other device information to that user (e.g., data indicative of what the printer is currently printing, i.e., print data).

Embodiments of the device management infrastructure may also provide the capability to execute one or more applications to process device information received from one or more devices. These applications may execute internally to the device management infrastructure. For example, an application may receive data from a barcode scanner at a loading dock. As each incoming package is scanned, the application may look up data from the scanned barcode in a data table and update the location of the package in a database. The database may be maintained internally to the device management infrastructure. In contrast, embodiments may also include the ability to notify applications external to the device management infrastructure. For example, the device management infrastructure may implement an API (e.g., a Representational State Transfer (REST) API) for communication with one or more applications or devices external to the device management infrastructure.

The term "device information" should be understood to refer to any electronic data and/or signals that may be sent or received from an electronic device. For example, device information may include electronic data packets that reference a device state, such as the device's settings, firmware, or software. The device information may also include data received from one or more sensors (e.g., motion sensors, bar code readers, device diagnostic sensors, GPS sensors, radio frequency identifier tag readers, cameras, battery monitors, consumable monitors, or the like) coupled to or associated with a device in communication via a device management infrastructure. Further examples of device information may include, but are not limited to, product inventory levels, device battery readings, device error conditions, print data, device consumable media levels, location information, image data, audio data, motion sensor readings, RFID and/or NFC tag information, bar code scan information, or the like. The device information may also be information sent to a device like an actuator position, a desired temperature, information to be displayed, information to be printed, radio frequencies, a motor speed, conveyor belt position settings, engine shutdown commands, local and/or remote temperatures, a measured humidity, a measured pressure, infrared sensing information, ultrasonic sensing information, or the like. In some embodiments, the device information may include commands, such as configuration settings, instructions to perform certain actions, or the like.

The term "device" should be understood to refer to any object that is instrumented with electronic systems operable to exchange device information with and/or be managed by the device management infrastructure. Devices may be associated with particular sets of permissions, such as associated with particular users or organizations as described above. In some embodiments, particular users may have administrative rights to control access to particular devices via the device management infrastructure. In some embodiments, devices may include one or more components that separately report device information. It should be readily appreciated that the distinction between a device and a component may be different in different contexts. These different contexts may be presented via an interface, such as a web-based device dashboard, a device management application, or the like, although it should be appreciated that the context may also be defined by other means than a user interface (e.g., based on a relationship between a particular component and a particular application). For example, a factory manager may be presented with device information for a particular manufacturing equipment as a single device when viewing the manufacturing equipment in a web-based dashboard, while a repair technician tasked with maintenance of the particular manufacturing equipment may be presented with the same manufacturing equipment as multiple devices (e.g., cooling system, power supply, main processor, etc.). In the context of this application, the term device should be understood to refer to devices managed by the device management infrastructure. For example, an external accounting, database, or ERP system that communicates with the device management infrastructure but is not managed by the device management infrastructure and does not report device information to the device management infrastructure would not qualify as a "device" under the definition of device as used herein.

Devices may be categorized as "edge devices" and/or "legacy devices". The term "edge device" should be understood to refer to any device that is managed by the device management infrastructure and capable of direct communication with the device management infrastructure according to one or more communication protocols associated with the device management infrastructure. Devices that contain communications modules operable to communicate with a management server in a device-agnostic format (e.g., via a device management API supported by the management server) can be considered edge devices. These edge devices may include one or more software applications or device drivers to facilitate communication in the device-agnostic format, such as by generating one or more messages containing the device information for transmission in the device-agnostic format. Example edge devices may include, but are not limited to, network-enabled printers capable of communicating via the device management infrastructure in the device-agnostic format, laptops, desktops, smartphones, or tablet computers executing an application or driver to communicate via the device management infrastructure in the device-agnostic format, or any other device capable of direct communication via a device-agnostic format and using the device management infrastructure.

In contrast with the edge devices, the term "gateway devices" is used to refer to bridge devices that enable one or more "legacy devices" to communicate via the device management infrastructure. Gateway devices may serve to perform a protocol translation to translate device information provided in a device-native format into the device-agnostic format used throughout the device management infrastructure. The term "legacy device" may refer to any device that is configured to communicate in a device-native format instead of a device-agnostic format used by the device management infrastructure. A gateway device may receive device information from a legacy device in the device-native format, and an application executing on the gateway device may translate the device information into a device-agnostic format. It should be appreciated that translation from a device-native format to a device-agnostic format may not require a translation in communication protocols. For example, a legacy device may communicate device information to a gateway device via one or more data packets sent using Internet Protocol (IP), with the contents of the data packets presented in the device-native format. The gateway device may receive these data packets and reformat the contents to generate one or more IP packets containing the device information formatted in the device-agnostic format.

It should further be appreciated that a device may possess the capability to connect to a device management infrastructure as both an edge device and a legacy device. For example, a device may ship to a customer containing circuitry configured to connect both directly to the device management infrastructure (e.g., as an edge device), and via a gateway device (e.g., a legacy device). As a specific example, one such device could be a printer implemented to communicate via both a native printer language format (e.g., Zebra Programming Language (ZPL)), and with the cloud via a device-agnostic format. The native printer language format might be received and processed by a gateway device to communicate with the device management infrastructure, or the printer may communicate directly with the device management infrastructure as an edge device. In some embodiments, devices that are capable of operating as both an edge device and a legacy device may be configured by a purchaser or user to select how to communicate with other devices and with a device management infrastructure.

The term "interface" should be understood to apply to connections used to provide access to device information gathered via the device management infrastructure. Examples of interfaces may include web-based device dashboards (e.g., a web page associated with a particular device, group of devices, or the like), APIs used to communicate with external applications (e.g., an API interface for communication with a customer database not managed by the device management infrastructure), and/or an external application communicating via an API.

It should also be appreciated that there may be some overlap between edge devices, gateway devices, and interfaces. For example, a gateway device (e.g., a router configured to translate data received from connected device into a device-agnostic format) may also be managed by the device management infrastructure, and thus function as an edge device. Such a gateway device may also provide an interface (e.g., a web server) allowing a user to access device information provided by the device management infrastructure. Similarly, in some embodiments a mobile phone may function as an edge device (e.g., by reporting the status of the mobile phone directly), a gateway device (e.g., by receiving Wi-Fi communication from nearby devices and translating such communications into a device-agnostic format for transmission to the device management infrastructure), and an interface (e.g., by providing a user with web browser access to a web-based device state dashboard hosted by the device management infrastructure or by running a native application).

The term "user" should be understood to refer to an individual associated with a particular set of account credentials for accessing the device management infrastructure. The term "organization" should be understood to refer to an entity that may include multiple users. Devices may be associated with specific users and/or organizations. For example, a particular business may have an organization set up via the device management infrastructure, and all of the business's devices may be associated with the organization. Individual users associated with the business may be given separate user accounts and associated with the organization. In some embodiments, the device management infrastructure provides for role-based management of users within organizations. For example, an organization administrator may assign particular devices to particular users for access, management, and the like. It should be appreciated that an organization administrator may have control over managing access to any and all devices and applications owned or managed by the organization.

The term "world" is used to refer to the set of all devices, applications, and other entities to which a particular user or organization has access to within the device management infrastructure at any one particular time. As such, the world associated with a particular user may encompass all entities managed by the device management infrastructure that are visible to the user, such as devices to which the user has specifically been granted access by others, public devices, devices owned by the user, and the like. Any one user may have access to a multiplicity of worlds. At minimum the user will have access to his "home world" which refers to the user's account which he created when joining the service. Additionally there may be a "public world" which encompasses all devices and entities that all users have chosen to make publicly available to all other users. Additionally, users may choose to create "private" or "semi-private" worlds, and invite or offer access to other users to these worlds. Users may be able to add subsets of devices they have access to, called "Groups", to these worlds, thereby creating a plurality of subsets of devices and entities that various sets of users have access to and can collaborate with. In some embodiments, whether a device is a member of a particular group is based on who is responsible for maintaining, servicing, updating, possessing, or using the device. Groups may be dynamic, such that devices or applications are automatically added or removed from groups based on rules and/or based on dynamically changing device information. In some embodiments, groups are used to determine which devices are within a given world, such as if the world is defined as containing a certain group, as devices are added to that certain group, they are also added to the world.

The term "healthcare organization" is used to refer to any practice, clinic, hospital, emergency facility, out-patient surgery center, or other location used for the purpose of providing medical treatment to patients. A healthcare organization may also include a grouping of a plurality of these locations, such as a single system that includes multiple hospitals, a clinic and hospital in affiliation with one another, or the like. Healthcare organizations may also include mobile treatment centers, ambulances, and the like. For example, in some embodiments an ambulance that picks up a patient and brings the patient to a hospital and the hospital itself could be considered as part of a single healthcare organization.

Healthcare organizations may employ a plurality of healthcare information systems. As used herein, the term "healthcare information system" should be understood to refer to any electronic system used to store electronic information relating to patients, including but not limited to hospital Admission-Discharge-Transfer (ADT) systems, Electronic Health Records (EHR) systems, Picture Archiving and Communications Systems (PACS), and the like.

As used herein, the term "beacon" should be understood to refer to any device capable of broadcasting a particular signal, instruction, or other data that identifies the device to local systems listening for the beacon. The term "beacon" may include, for example, Bluetooth Low Energy (BLE) beacons.

System Architecture

The method, apparatus, and computer program product of the present invention may be embodied by any of a variety of components. For example, the method, apparatus, and computer program product of an example embodiment may be embodied by networked equipment, such as a server or other network entity, configured to communicate with one or more components, which may include one or more edge devices, gateway devices, interfaces, or the like. Additionally or alternatively, the components may include fixed computers, such as a personal computer or a computer workstation. Still further, example embodiments may be embodied by any of a variety of mobile terminals, such as a portable digital assistant (PDA), portable data terminals (PDTs), sensors, readers, mobile telephone, smartphone, laptop computer, tablet computer, or any combination thereof.

FIG. 1 discloses an example device management infrastructure 100 within which embodiments of the present invention may operate. The device management infrastructure 100 may include a management server 102 in communication with one or more edge devices 110A-110N, one or more gateway devices 112A-112N and one or more interfaces 116A-116N.

The management server 102 may provide various applications, interfaces, tools, and utilities to manage, access, interact with, communicate with, and process information from edge devices 110A-110N, gateway devices 112A-112N, and interfaces 116A-116N. The management server 102 may be implemented in a "cloud" environment, whereby the management server 102 is located remotely from one or more of the edge devices 110, gateway devices 112, and interfaces 116. In some embodiments, the edge devices 110, gateway devices 112 and/or interfaces 116 are owned and/or operated by a different entity than the management server 102. For example, a business may own several edge devices 110 and gateway devices 116 that provide data to the management server 102, while the management server 102 is owned and/or maintained by a management company other than the business.

In some embodiments, users may purchase or lease access to the management server 102. For example, a user may pay a fee to access device management services offered by the management server 102. The fee may be determined based on a time duration (e.g., monthly, weekly, or annually), based on a number of devices managed (e.g., a fee that increases per device in communication with the management server 102), based on a number of users who have access to the account, or the like.

The edge devices 110A-110N may include various devices capable of directly providing information via the device management infrastructure 100. For example, edge devices may include, but are not limited to, various electronic devices configured to communicate with the device management server 102 via a device-agnostic protocol. Examples of these devices may include such as cellular phones, network routers, laptop computers, tablet computers, network-enabled printers, network-enabled laminators, radio frequency identifier (RFID) readers, barcode scanners, netbooks, or the like. In some embodiments, the edge devices 110 may execute one or more applications to facilitate communication via the device management infrastructure 100. For example, the edge devices 110 may include a driver program or middleware program that generates messages in a device-agnostic format readable by the management server 102.

The gateway devices 112A-112N may include devices operable to enable one or more legacy devices 114A-114N to communicate with the device management infrastructure. To enable this communication, a gateway device 112 may receive device information in a device-native format, translate device information to a device-agnostic format, and transmit the translated data to the management server 102. For example, a data structure used to send settings to a printer might have the following structure:

TABLE 1

```
{
  "attributes":{
    "qln320.set.back.feed":"NO_BACKFFED",
    "q.ln320.set.darkness":"10",
    "qln320.set.label.width":"50",
    "qln320.set.media.feed.options":"NO_FEED",
    "qln320.set.media.handling":"TEAR_OFF",
    "qln320.set.media.type":"GAP_NOTCH",
    "qln320.set.speed":"1",
```

TABLE 1-continued

```
    "qln320.set.tear.off.adjust":"0",
  },
}
```

And a data structure used to register a device and create a new virtual device model for management via the device management infrastructure might have the following structure:

TABLE 2

```
{
  "attributes":{
    "qln320.dyn.prop.location":"Chicago Office",
    "qln320.dyn.prop.name":"West Wing Printer",
    "qln320.stat.prop.serial.number":"ABC124568974"
  },
  "avatarDefinitionId":3
}
```

The interfaces 116A-116N may include various systems and components for accessing and viewing data provided via the device management infrastructure. These interfaces 116 may include systems operable to view information generated by the device management infrastructure, such as a web browser used to view a web-based portal application. For example, the interfaces 116 may include cellular phones, network routers, laptop computers, tablet computers, or netbooks. Some types of information generated by the device may be communicated with a buzzer, message, or sounds via a speaker; with light via a LED, screen, or industrial lighting system, or printed output from a printer, copier, message board, or facsimile machine. In some embodiments, the interfaces 116 may include external systems or applications designed to interface with the device management infrastructure via an API, such as a REST API. For example, the interfaces 116 may include application servers external to the device management infrastructure, such as external ERP systems, database systems, or the like.

The management server 102 may access a permissions database 106 for routing of data throughout the device management infrastructure 100. The permissions database 106 may define access permissions for the edge devices 110, gateway devices 112, legacy devices 114, and/or interfaces 116. For example, each edge device 110, gateway device 112, and legacy device 114 may be owned and/or managed by a particular user account identified in the permission database. The user account may specify which other edge devices 110, gateway devices 112, legacy devices 114 interfaces 116, and/or user accounts may access data provided by an edge device or legacy device owned by the user account. Device permissions may be set for particular types of data provided by each device. For example, a printer may provide error condition information, consumable level information, and data indicating the content of the document the printer is currently rendering for printing. An owner of the printer may allow another user (e.g., a printer maintenance service) to access the error condition information and consumable level information, but not the print data or content.

In some embodiments, the permission database 106 may include one or more group definitions. Group definitions may categorize devices into particular groups with particular access levels. For example, users may have access to particular groups, and the groups may be determined dynamically. In some embodiments, users or organizations may freely configure one or more groups and may publish such groups (e.g., make them accessible) to one or more third parties (i.e., other users or organizations within the device management infrastructure).

Returning to the printer example provided above, a group may be established for "printer devices with error conditions". Upon providing data to the management server 102 that a particular printer device is experiencing an error condition, the printer device may be added to the "printer devices with error conditions" group. A printer maintenance service may have access to device information provided by any device that has been added to the "printer devices with error conditions" group, such that when the printer receives an error condition, the printer maintenance service is provided with access to the status of the printer so they can attempt to remediate the error. In some embodiments, once the printer maintenance service services one or more printers having error conditions (i.e., addresses such error conditions), the one or more printers are removed from the "printer devices with error conditions" group.

It should be readily appreciated that device information can be routed according to various other dynamically defined groups. As another specific, non-limiting example, a scanner (e.g., a barcode scanner or RFID reader) may register that a good has been dropped off with a common carrier for delivery to a destination. Upon receipt of the good, the scanner device may notify the management server, and a device (e.g., a radio frequency identification tag) associated with the good may be added to a group including all of the items present within the shipment being made by the common carrier. An owner or operator of the common carrier may be provided with access to this group to monitor the items they are shipping. When the goods are delivered to their final destination, the management server 102 may be notified (e.g., by scanning the radio frequency identifier tag again at the destination by another scanner device), and access may be removed from the common carrier.

The operations of the management server 102 may be enabled by a device management system 104. The device management system 104 may include hardware and/or software to facilitate the operations of the management server 102. For example, the device management system 104 may serve to facilitate user authentication services, management of device permission settings, hosting of a web portal for interfacing with the management server 102, operating a publish/subscribe system for transferring data throughout the device management infrastructure 100, providing a REST API for interfacing with external systems, and/or any other functionality necessary to support the device management infrastructure 100.

The management server 102 may be embodied by a computing system, such as the apparatus 200 shown in FIG. 2. As illustrated in FIG. 2A, the apparatus 200 may include a processor 202, a memory 204, input/output circuitry 206, communications circuitry 208, credentialing circuitry 212, application management circuitry 214, and device model management circuitry 216. The apparatus 200 may be configured to execute the operations described above with respect to FIG. 1 and below with respect to FIGS. 3, 5-8, and 17-20. Although these components 202-216 are described with respect to functional limitations, it should be understood that the particular implementations necessarily include the use of particular hardware. It should also be understood that certain of these components 202-216 may include similar or common hardware. For example, two sets of circuitry may both leverage use of the same processor, network interface, storage medium, or the like to perform their associated functions, such that duplicate hardware is not required for each set of circuitry. The use of the term "circuitry" as used herein with respect to components of the apparatus should therefore be understood to include particular hardware configured to perform the functions associated with the particular circuitry as described herein.

The term "circuitry" should be understood broadly to include hardware and, in some embodiments, software for configuring the hardware. For example, in some embodiments, "circuitry" may include processing circuitry, storage media, network interfaces, input/output devices, and the like. In some embodiments, other elements of the apparatus 200 may provide or supplement the functionality of particular circuitry. For example, the processor 202 may provide processing functionality, the memory 204 may provide storage functionality, the communications circuitry 208 may provide network interface functionality, and the like.

In some embodiments, the processor 202 (and/or co-processor or any other processing circuitry assisting or otherwise associated with the processor) may be in communication with the memory 204 via a bus for passing information among components of the apparatus. The memory 204 may be non-transitory and may include, for example, one or more volatile and/or non-volatile memories. In other words, for example, the memory may be an electronic storage device (e.g., a computer readable storage medium). The memory 204 may be configured to store information, data, content, applications, instructions, or the like, for enabling the apparatus to carry out various functions in accordance with example embodiments of the present invention.

The processor 202 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 202 may be configured to execute instructions stored in the memory 204 or otherwise accessible to the processor. Alternatively or additionally, the processor may be configured to execute hard-coded functionality. As such, whether configured by hardware or software methods, or by a combination thereof, the processor may represent an entity (e.g., physically embodied in circuitry) capable of performing operations according to an embodiment of the present invention while configured accordingly. Alternatively, as another example, when the processor is embodied as an executor of software instructions, the instructions may specifically configure the processor to perform the algorithms and/or operations described herein when the instructions are executed.

In some embodiments, the apparatus 200 may include input/output circuitry 206 that may, in turn, be in communication with processor 202 to provide output to the user and, in some embodiments, to receive an indication of a user input. The input/output circuitry 206 may comprise a user interface and may include a display and may comprise a web user interface, a mobile application, a client device, a kiosk, or the like. In some embodiments, the input/output circuitry 206 may also include a keyboard, a mouse, a joystick, a touch screen, touch areas, soft keys, a microphone, a speaker, or other input/output mechanisms. The processor and/or user interface circuitry comprising the processor may be configured to control one or more functions of one or more user interface elements through computer program instructions (e.g., software and/or firmware) stored on a memory accessible to the processor (e.g., memory 204, and/or the like).

The communications circuitry 208 may be any means such as a device or circuitry embodied in either hardware or a combination of hardware and software that is configured to receive and/or transmit data from/to a network and/or any other device, circuitry, or module in communication with the apparatus 200. In this regard, the communications circuitry 208 may include, for example, a network interface for enabling communications with a wired or wireless communication network. For example, the communications circuitry 208 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s).

The connection management circuitry 210 includes hardware that may be configured to support management of connectivity of one or more devices to the apparatus 200. The connection management circuitry 210 may include hardware that allows the apparatus to discover, register, establish communications with, and send data to and from devices that are in communication with the apparatus 200. To this end, the connection management circuitry 210 includes hardware for performing these functions, including but not necessarily limited to a processor and network interface hardware. The connection management circuitry 210 further includes or communicates with a memory for storing data relating to connected devices.

The credentialing circuitry 212 includes hardware that may be configured to manage access permissions and credentials for users and devices in communication with the apparatus 200. The credentialing circuitry 212 is responsible for determining which users, applications, and devices have access to data provided by particular applications and devices. To this end, the credentialing circuitry 212 may include hardware configured to apportion devices into particular groups and worlds, and to provide particular users and applications with access to the devices contained within those groups and worlds. To perform these functions, the credentialing circuitry 212 may include hardware for receiving requests to access data related to particular devices, hardware for managing user account data (e.g., user login and password information), hardware for maintaining and updating a set of permissions associated with users, groups, worlds, devices, and the like, and the like. For example, the credentialing circuitry 212 may include a processor, such as the processor 202, to manage and process requests to add, delete, and modify device permissions, user account data, and the like. Credentials, account information, and associations between devices and particular users, groups, or worlds may be stored in a memory, such as the memory 204.

The application management circuitry 214 includes hardware that may be configured to manage access to device information for one or more applications. The application management circuitry 214 may include hardware configured to provide an application programming interface allowing applications to access the device information. The application management circuitry 214 may provide applications with the ability to access data associated with particular devices, send data to those particular devices, receive and calculate statistics related to devices, and the like. The application management circuitry 214 may interact with the credentialing circuitry 212 to determine whether particular applications are allowed to access data received from particular devices. The applications that communicate with the application management circuitry 214 may execute locally on the apparatus, remotely on a remote computer, or the like. In some embodiments, applications may be provided by an owner or maintainer of the apparatus 200. In some embodiments, applications may additionally or alternatively execute remotely and interact with the device information via an application programming interface. The application management circuitry 214 may include a processor, such as the processor 202, for executing local applications and responding to inquiries and requests from remote applications. The application management circuitry 214 may further include a memory, such as the memory 204, for storing data associated with applications, device information accessible to the applications, and the like. In some embodiments, the application management circuitry 214 may interact with the device model management circuitry 216 to obtain device information, prompt configuration changes to devices, and the like.

The device model management circuitry 216 includes hardware that may be configured to manage one or more device models, to allow applications, devices, and users to interact with the device model and to propagate changes made to the device models. In some embodiments, the device model management circuitry 216 includes hardware configured to update the status of the device model based on data received from devices in communication with the apparatus 200. In some embodiments, the device model management circuitry 216 may provide a framework and/or API that allows users, applications, and other devices to affect changes to devices in communication with the apparatus 200 by making changes to the device model. For example, the device model management circuitry 216 may identify interactions with the device model by applications, users, devices, and the like, determine configuration changes for the device associated with the device model in response to the identified interactions, and transmit the configuration changes or otherwise cause the configuration changes to the device associated with the device model based on the determined configuration changes. To perform these functions, the device model management circuitry 216 may include a processor, such as the processor 202. The device models may be maintained by the device model management circuitry 216 using a memory, such as the memory 204. Changes may be propagated to the devices using a network interface, such as provided by the communications circuitry 208.

The gateway device(s) 218 may be embodied by one or more computing systems, such as apparatus 218 shown in FIG. 2B. As illustrated in FIG. 2B, the apparatus 218 may include a processor 220, a memory 222, input/output circuitry 224, device communications circuitry 226, and management server communications circuitry 228. The apparatus 218 may be configured to execute the operations described below with respect to FIGS. 1, 4, 5-8, and 18. The functioning of the processor 220, the memory 222, and the input/output circuitry 224 may be similar to the similarly named components described above with respect to FIG. 2A. For the sake of brevity, additional description of these components is omitted.

The gateway device 218 may include separate circuitry for communication with devices and with the device management server, represented as the device communications circuitry 226 and the management server communications circuitry 228, respectively. The device communications circuitry 226 may include hardware configured to communicate with devices proximate or otherwise locally accessible to the gateway device via a device-specific protocol, and the management server communications circuitry 228 may be configured to communicate with a management server located remotely via a device-agnostic protocol. For example, the device communications circuitry 226 may include hardware for communicate with local devices via infrared, radio frequency identification (RFID), Bluetooth, ZigBee, or the like. Although the device communications circuitry 226 may typically communicate via short range or line-of-sight protocols such as those described above, it should be appreciated that the device communications circuitry 226 may employ any protocol for communicating with devices.

The management server communications circuitry 228 includes hardware configured to communicate with a management server via a device-agnostic format. For example, the apparatus 218 may translate data received in a device-specific or short range protocol, and package the data for transmission to the management server and receive data from the management server by transmission control protocol (TCP) or the like.

As will be appreciated, any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

It is also noted that all or some of the information presented by the example displays discussed herein can be based on data that is received, generated and/or maintained by one or more components of apparatuses 200 and 218. In some embodiments, one or more external systems (such as a remote cloud computing and/or data storage system) may also be leveraged to provide at least some of the functionality discussed herein.

As described above and as will be appreciated based on this disclosure, embodiments of the present invention may be configured as methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Example Device Management Data Flow

Referring now to FIG. 3, a block diagram is illustrated showing an example device management server 300 in accordance with embodiments of the present invention. The device management server 300 may provide for management of a device management infrastructure, such as the device management infrastructure 100 described above with respect to FIG. 1. Example embodiments of the device management server 300 may include the device management system 104 and the apparatus 200 described above.

The device management server 300 may interface with one or more external applications 302, devices 304, external connections 306, and users 308. The device management server 300 may comprise one or more virtual device models 310. The virtual device modules 310 may serve as a representation of the status of the device as known to a device management infrastructure. For example, each device in communication with the device management server 300 may have an object representation in a memory or database. The virtual device models 310 may also be used to generate a graphical representation of the device status, such as a web portal interface providing the device information.

In some embodiments, the virtual device models 310 may be accessed by one or more internal applications 312 to provide information to the internal applications and to allow the internal applications 312 to interact with the devices 304. In some embodiments, a user may provide or configure one or more of the internal applications 312 for use within the device management server 300. Example internal applications may include a device "dashboard" that is visible in a web browser interface to display data associated with the virtual device model. Other example internal applications may include applications for monitoring and presenting statistics related to the devices as derived from the virtual device models, and/or other applications for analyzing, processing, and/or packaging device information derived from the virtual device models 310.

The device management server 300 may provide users with the ability to host certain applications designed to send and receive data via a device management infrastructure. For example, a user may use the device management server 300 to execute an inventory management application that receives data from one or more sensors within a warehouse to monitor stock on hand.

In some embodiments, the internal applications 312 may connect with one or more devices or applications. For example, the inventory management application described above may be configured to interact with a business storefront to receive orders, generate invoices, and direct the shipment of goods from the warehouse. In some embodiments, the internal applications 312 may function as data aggregators. For example, if a particular device or devices are configured to provide device information to the public, then an analysis application may aggregate device information from all similar devices to perform analytics tasks. For example, certain users may elect to have supply chain transit times made publicly available to assist other users with estimating transit times using certain common carriers. It should be appreciated that some data may be obfuscated or redacted (e.g., the exact contents of customer shipments) in order to protect confidential company, customer, and user information. As another example, manufacturers may wish to receive aggregated error information (e.g., barcode scanner error rates) to identify possible software defects and opportunities for product improvement. As yet another example, maintenance personnel may receive information aggregated from multiple devices that indicate which devices are in need of maintenance. As a further example, RFID readers may be used to sense the arrival of goods, and this data may be coupled with temperature sensor data gathered from inside the shipping container in which the goods were delivered to indicate the arrival time as well as condition of the shipment.

The device management server 300 may further include management applications designed to facilitate the administration and operation of the device management infrastructure. For example, the device management server 300 may include a connection management module 314, a system management module 316, and a user and organization management module 318.

The connection management module 314 may facilitate connections between the device management server 300 and the various devices and interfaces external to the device management server 300. In some embodiments, the functionality of the connection management module 314 is provided by the connection management circuitry 210 described above with respect to FIG. 2A. The connection management module 314 may, for example, configure the manner and frequency of device state reporting and polling, control routing of device state throughout the device management infrastructure, and the like. For example, reporting the status of a device may be a power-intensive task. As such, if an edge device is configured to report its state frequently, and the device operates from battery power, frequent reporting to update the virtual device model may drain the battery. Similarly, devices that operate under bandwidth constraints may also be adversely affected by frequent updating of the state of their attendant virtual device model. Therefore, the virtual device model may be configured to reduce a reporting interval in certain circumstances, such as if a device is operating from battery power or is otherwise bandwidth constrained. Similarly, the virtual device model may also be configured to induce a more frequent reporting interval if the attendant edge device is in a "charging state", or in response to the device being plugged into an outlet or recharging station. The connection management module 314 may also detect network congestion to determine a reporting interval. For example, in an environment with many devices reporting, increasing a device reporting interval may make communications on the network difficult. As such, the connection management module 314 may reduce a reporting interval for most devices to ensure network traffic is received in a timely manner. In the event a device experiences an error condition, the connection management module 314 may increase the reporting frequency of the device in an error state to allow for easier troubleshooting.

The system management module 316 may operate to control the different elements of the device management server 300, such as configuration and execution of the processes necessary to control the functionality of the device management server 300. In some embodiments, the functionality of the system management module 316 is provided by the device model management circuitry 216 and/or the application management circuitry 214 described above with respect to FIG. 2A. The system management module 316 may act to ensure that data is properly routed between other modules, it may ensure that subsystems are working properly and restarted when necessary, and it may make sure that the system loads are balanced between modules to ensure efficient and robust operation.

The user and organization management module 318 may be operable to maintain and edit the access permissions associated with the users, organizations, devices, and groups communicating via the device management infrastructure. In some embodiments, the functionality of the user and organization management module 318 is provided by the credentialing circuitry 212 described above with respect to FIG. 2A. The user and organization management module 318 may function to determine which devices and groups belong to which users, organizations, and the like, and to control how data is provided to authorized parties. In some embodiments, the user and organization management module 318 may be operable to control which devices are added and removed to which groups, in addition to determining access by users and applications to those groups. For example, a given corporation may be associated with an organization, and employees of the corporation may each have independent user accounts. An administrator associated with the corporation may define which corporation user accounts have access to which particular devices, applications, groups, and the like. When a user leaves the corporation, the administrator may revoke the user's access. In some embodiments, access is defined based on certain roles associated with the user (e.g., a job title), such that multiple devices, applications, or groups may be reassigned to a different user by associating the different user with the appropriate role (e.g., a quality control manager may have certain baseline access rights to various devices).

The device management server 300 may further include connections to external applications 320, connections to devices 322, and connections to users 324. The connections to external applications 320 may include connections to applications executing on computing nodes external to the device management infrastructure. For example, the connections to external applications may be facilitated using a REST API to enable other systems (e.g., client ERP systems) to send and receive data via the device management infrastructure. In some embodiments, communication is implemented using JavaScript® Object Notation (JSON) via a REST API. In some embodiments, communication is implemented using Constrained Application Protocol (CoAP). The connections to devices 322 may include connections to the edge devices, and gateway devices such as described above with respect to FIGS. 1 and 2.

In some embodiments, the interface to user portal applications (e.g., a graphical display of data received by the device management server) is provided via connections to users 324. The connections to users 324 may include applications configured to provide a web-based portal interface allowing a user to view the status of a particular device or devices. Each of the connections to devices, applications, and users external to the device management server 300 may be facilitated by one or more APIs. For example, these connections may include APIs for communication with applications executing via the device management server (e.g., "internal" applications), APIs to establish device properties and methods, device management APIs, device discovery APIs, user and account management APIs, and security and authentication APIs. The various APIs may be structured similarly. For example, each API may be are embodied as one or more HTTP REST calls, which use JSON payloads when necessary. The API function calls may be used to perform Create, Read, Update, Delete, Execute, and Owner (CRUDXO) functions using HTTP POST, PUT, GET, and DELETE functions. Depending upon the details of the specific call, all the functions of the different modules can be executed.

Example Device Gateway

FIG. 4 depicts a block diagram of an example of a device gateway 400 in accordance with example embodiments of the present invention. The device gateway 400 is an example of a gateway device 112 as described above with respect to FIG. 1 and the apparatus 218 as described above with respect to FIG. 2B. The device gateway 400 may provide a bridge to allow one or more legacy devices to communicate with a central server or cloud implementing a device management infrastructure. For example, a user may have several legacy devices that are configured to communicate with one another via a wireless network via device-native format, but which are not configured to interface directly with a remote server implementing a device management infrastructure in a device-agnostic format. The device gateway 400 may function to receive information from these legacy devices, and package and transmit the data in a device-agnostic format suitable for use by the remote server. As a specific example, a user may wish to track product inventory levels in a supply rack using RFID tag readers. The RFID tag readers may be configured to read RFID tags of items removed from the supply rack, and report the identity of the RFID tags over a network in a format specific to the RFID tag readers. An example device gateway 400 might receive the item tag information from these RFID sensors, and package and transmit the data to a remote server in a device-agnostic format.

The device gateway 400 may communicate with one or more devices 404 via various network protocols. In some embodiments, the communication functionality of the device gateway 400 with respect to devices is provided by device communications circuitry 226 as described above with respect to FIG. 2B. For example, the device gateway 400 may communicate with the devices 402 over a wireless protocol, such as the IEEE 802.11 family of protocols. The device gateway 400 may process data received from the one or more devices 402 (e.g., the legacy devices 114 described with respect to FIG. 1), and transmit the data to a cloud software application 404, such as the device management server described above with respect to FIGS. 1-3. The device gateway 400 may communicate with the device management server using management server communications circuitry 228 as described above with respect to FIG. 2B.

The device gateway 400 may include one or more internal applications 406, a device discovery and management module 408, and a connection module 410 for communicating with devices 402. The device gateway 400 may further comprise a connection management module 412, a system management module 414, a security module 416, and a connection module for communicating with a cloud application 418.

The internal applications 406 may refer to various applications that execute on the device gateway 400 to receive and process data prior to transmission to either the devices 402 or the cloud 404. Execution of the internal applications may be performed by a processor, such as the processor 220 described above with respect to FIG. 2B. For example, the internal applications 406 may include applications to aggregate data received from multiple devices prior to transmission to the cloud 404, or applications configured to convert messages received from the cloud 404 to a format suitable for managing the devices. In the context of the device gateway, the internal applications 406 may refer to application specific code resident on the gateway which is optionally loaded when the gateway needs to execute some special functions needed only by a specific application. For example, a gateway may execute an application to filter RFID reads coming from an RFID reader. Such an application may be loaded only on gateways that are associated with RFID readers need this code.

The device discovery and management module 408 may be configured to detect local devices and register the detected devices with the cloud 404. Discovery and management of local devices may be performed by device communications circuitry 226 as described above with respect to FIG. 2B. The device discovery and management module 408 may be used to discover devices on a network in a variety of different ways. For example, a device will broadcast its presence and compatible devices may respond with identity information that allows the device to establish a connection. In some embodiments, the gateway device may employ several methods to detect all compatible devices. In some embodiments, the gateway may be loaded with a priori data via the cloud to establish this connection.

The connections to devices 410 may be performed according to various protocols, including but not limited to Bluetooth, the IEEE 802.11 protocol suite, ZigBee, or any other network protocol suitable for communication between electronic devices. It should be appreciated that while such communication may generally be performed wirelessly, the device gateway may also be configured for wired communication and other direct communication methods.

The connection management module 412 may be operable to facilitate communication among the devices 402, the device gateway 400, and the cloud 404. As above, connections between devices and the device gateway 400 may be provided by device communications circuitry 226, and connections to the device management server may be provided by the management server communications circuitry 228 as described above with respect to FIG. 2B. In some embodiments, the connection management module 412 is configured to interface with a device management server over a network. In some embodiments, this communication may be performed via a local network and Internet connection maintained by the user. Such local networks commonly implement firewalls to secure the local network from intrusion from external threats. As such, the connection management module 412 may provide various features, such as port-forwarding, network address translation, or the like for communicating through such a firewall. If a proxy server prevents the connection management module 412 from communicating with the device management server, the connection management module may be loaded with credentials prior to making the attempt to connect. These credentials may be loaded locally via computer with local access to the gateway.

The system management module 414 may ensure that the other modules are functioning properly. For example, the system management module 414 may ensure that modules are updated and restarted when necessary. If necessary, the system management module 414 may force the gateway to restart to reload global updates. The security module 416 may enable certain security protocols and privacy settings. For example, the security module 414 may ensure that only authorized devices are allowed to register with the device gateway 400 and communicate with the cloud 404. The security module may manage the encryption/decryption of data to/from the cloud, as well as ensure the appropriate use of certificates for this process. The functionality of the system management module 414 and the security module 416 may be provided by applications executing on a processor, such as the processor 220 described above with respect to FIG. 2B.

The connections to the cloud 418 may function to transmit device information received from the devices to a remote server located in a cloud operating environment, such as the management server 102 described with respect to FIG. 1. These connections may be provided by management server communications circuitry 226 as described above with respect to FIG. 2B.

Device Communications Data Flow

FIG. 5 is a logical data flow diagram 500 illustrating example communications among one or more devices 502, a platform 506, and one or more applications 510 in accordance with some example embodiments. The devices 502 may be edge devices 110 and/or legacy devices 114 as described above with respect to FIG. 1. These devices may provide information to a platform 506 (e.g., a device management server as described above with respect to FIG. 1) via a device API 504. In some embodiments, the device API 504 is provided by a gateway device 512, such as in the case where the devices 502 are legacy devices that are incapable of direct communication with the platform 506. In other embodiments, the devices 502 may communicate with the platform 506 via a set of library functions provided for this purpose in a device library 514. In some embodiments, the device library 514 provides a set of utilities and designs to assist an application developer with connecting a particular device to the platform 506.

The device library 514 may provide functions that allow a given device or associated application to "self-describe" the characteristics of the device, such as through the definition and use of a JavaScript Object Notation (JSON) data structure. In some embodiments, the device libraries 514 provide a framework that allows a software developer, user, or the like to specify the characteristics of the particular device to be stored and/or displayed in a virtual device model associated with the device as managed by the platform 506. In some embodiments, the device library 514 may include functions operable to interface with the logic of an application developed by a manufacturer or owner of a device that enable the device to connect to the platform, disconnect from the platform, receive instructions from the platform, read device information from the platform, write data to the platform, or the like. In some embodiments, these functions are provided via an embedded programming language, such as Embedded C.

Applications 510 may interact with the platform 506 via an application API 508. The platform 506 may expose the application API 508 and allow applications to obtain device information for which the particular application has appropriate credentials. For example, a given application may be associated with a particular user, group of users, or the like that have access to a particular device or group of devices. The application API 508 may allow applications to read data from and write data to any device to which the application has appropriate access credentials. In some embodiments, the application API 508 is provided as a REST API.

Example Device Group Organization

FIG. 6 illustrates a device grouping 600 in accordance with example embodiments of the present invention. As described above with respect to FIGS. 1-5, one benefit that may be derived from using some embodiments of a device management infrastructure as described herein is the ability to organize disparate devices into various groups with separate access permissions. The device grouping 600 illustrates one use of such device organization techniques.

The present example provides a set of printers that are remote devices 602 in communication via a device management infrastructure, such as described above with respect to FIGS. 1-5. The set of remote printers 602 are associated with three separate user accounts, Client A 604, a printer maintenance service 606, and Client B 608. Each of these user accounts is provided with access to a particular group of printers. In the present example, Client A 604 has access to the group of printers owned by Client A 610, and Client B 608 has access to the group of printers owned by Client B 614. A third grouping of printers also exists, a group of printers in need of maintenance 612, to which access is provided to the printer maintenance service 606.

In the present example, if Client A 604 were to access a web portal provided by the device management infrastructure, Client A 604 would be permitted to access representations of status information received from each of the printers in the group 610 owned by Client A. Similarly, for Client B 608 and the printer maintenance service 606, the device management infrastructure may provide a web-based interface for accessing each of the associated printer groupings.

Additionally, the device management infrastructure may also provide for dynamic group assignment and association. For example, if one of the printers in Client B's grouping suffers an error state, that printer may report the error state to a remote server via the device management infrastructure. In response to detecting the error state, the remote server (or an application executing thereon), may assign the printer to the group of printers in need of maintenance. Upon assigning the printer to the group of printers in need of access, the remote server may provide the printer maintenance service 606 with access to the newly failed printer. In this manner, various implementations of rule-based access permissions may be implemented via the device management infrastructure based on status information received from devices in communication via the device management infrastructure. It should be appreciated that the printer maintenance service may be provided with access to printers from more than one owner (e.g., both Client A and Client B) within the same group.

As an alternative embodiment, an example device group organization may be implemented by the printer maintenance service 606 creating a world, and inviting each client to join that world (e.g., a "printer maintenance" world). Each client may add whichever printer(s) they wish to the "printer maintenance" world, and the owner of the "printer maintenance" world may then be provided with the capability to monitor each of the printers added to that world. The owner of the "printer maintenance" world may then create a group within the "printer maintenance" world called "printers in need of maintenance", with a rule to add each printer within the "printer maintenance" world to the newly created group when said printer experiences an error condition (e.g., based on a particular result from a particular sensor on the printer).

Example Multi-Tenant Device Management Infrastructure

Figure 7A:
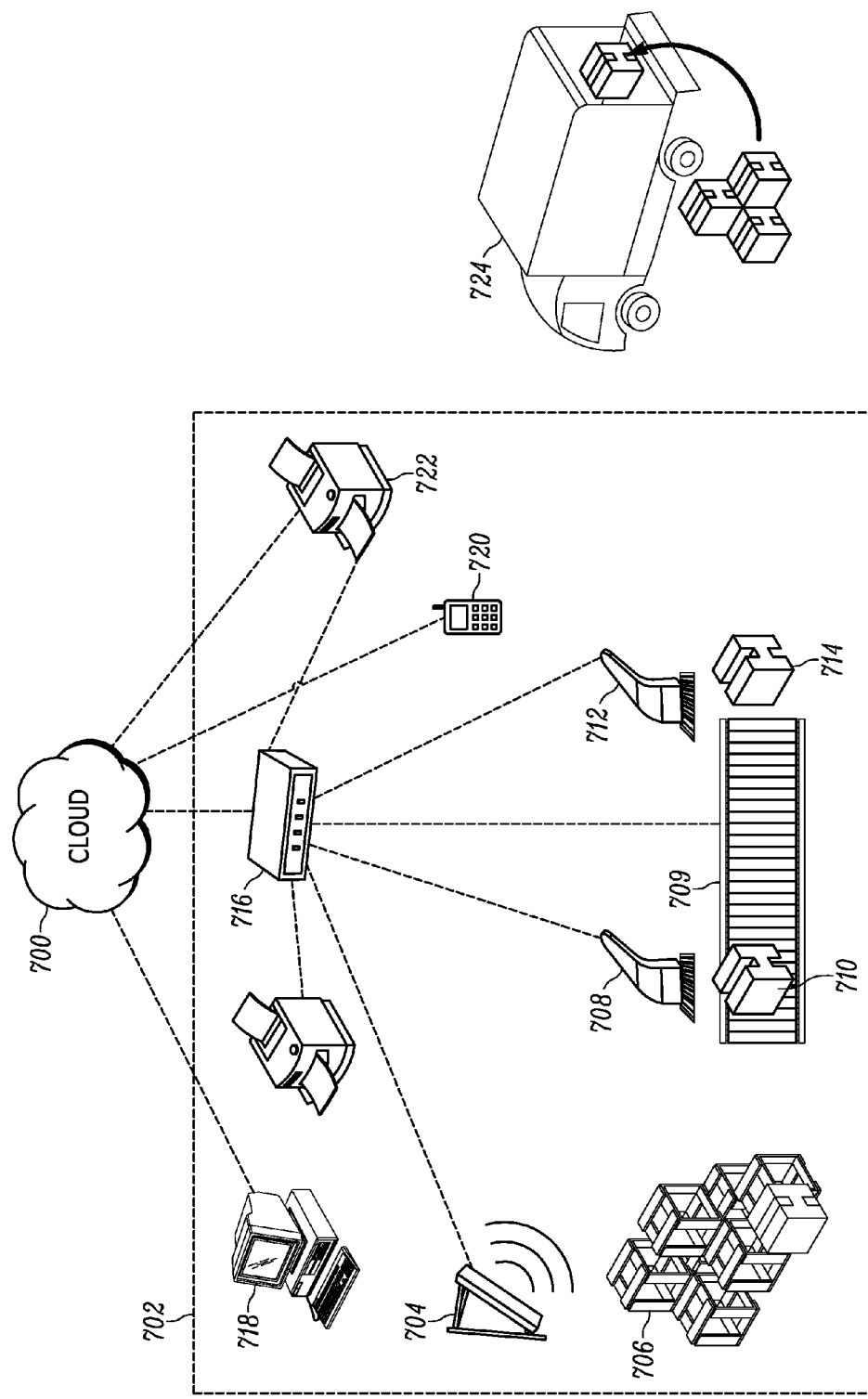

FIGS. 7A-7D illustrate an example multi-tenant device management infrastructure provided in accordance with embodiments of the present invention. These figures illustrate the implementation of a device management infrastructure supporting different device groups and worlds in an ERP system. FIG. 7A depicts the interaction among devices associated with a manufacturer's world 702 during a shipping process.

In the present example, the manufacturer's world 702 includes one or more RFID scanners 704, barcode scanners 708, 712, computer nodes 718, mobile devices 720, printers 722, and conveyor belts 709. The manufacturer's world 702 may also include one or more gateway devices 716 to allow legacy devices to communicate with a network cloud 700. The network cloud 700 may include a remote server for implementing one or more device management functions as described above with respect to FIGS. 1-5. It should be readily appreciated that the cloud 700 described with respect to FIGS. 7A-7D is intended to represent a single device management infrastructure. While this device management structure may include communication over known networks such as the Internet, the network cloud 700 is intended to represent communication with a particular device management infrastructure. While the manufacturer's world 702 depicted in FIG. 7A includes devices associated with a shipping process, the manufacturer's world 702 may also include various manufacturing devices, sensors, scanners, computers, and the like used throughout the acquisition of raw materials through generation of a finished product, which are not shown in FIG. 7A. In the present example, the printer 722 may be configured to communicate both directly with the device management infrastructure via the cloud 700, and also via the gateway device 716. For example, the printer 722 may communicate with the gateway device 716 according to a device-native format (e.g., Zebra Programming Language), and with the cloud 700 via a device-agnostic format (e.g., JSON). It should be appreciated that the printer 722 may be configured to communicate according to one format, the other format, or both formats via a processor. In some embodiments, the format used by the printer 722 to communicate with the cloud 700 is determined by a user of the printer 722, such as by a printer management menu.

A product inventory 706 may be monitored by one or more RFID sensors 704. For example, each product may be marked with an RFID tag and/or barcode to facilitate monitoring of the place of the product in the supply chain. When an order is received for a particular product (e.g., through a manufacturer computer system 718), a particular product may be removed from inventory and loaded onto a conveyor belt 709 for transport to a shipping bay. When the product is removed from inventory, the RFID sensor 704 may transmit a notification that the product has been removed to the device management infrastructure by communicating with the gateway device 716. An application executing within the device management infrastructure may reconcile the removal of the product against a customer order to perform inventory security and management functions.

Once the product 710 is placed on the conveyor 709, a barcode scanner 708 may report the barcode of the product 710 to the cloud 700. When the product 710 reaches the end of the conveyor at the shipping dock, another barcode scanner 712 may report that the product 714 is ready for shipping via a shipping service 724.

It should be appreciated that each of the devices 704, 708, 709, 712, 716, 718, 720, 722 present within the manufacturer's world 702 may report both states and error conditions of each device (e.g., whether the device is receiving an error condition) and any data acquired by device sensors (e.g., a barcode read by the barcode scanners 708, 712, or an RFID tag read by the RFID scanner 704). All of this device information may be reported to the cloud 700 for analysis, aggregation, processing, and reporting.

Figure 7B:
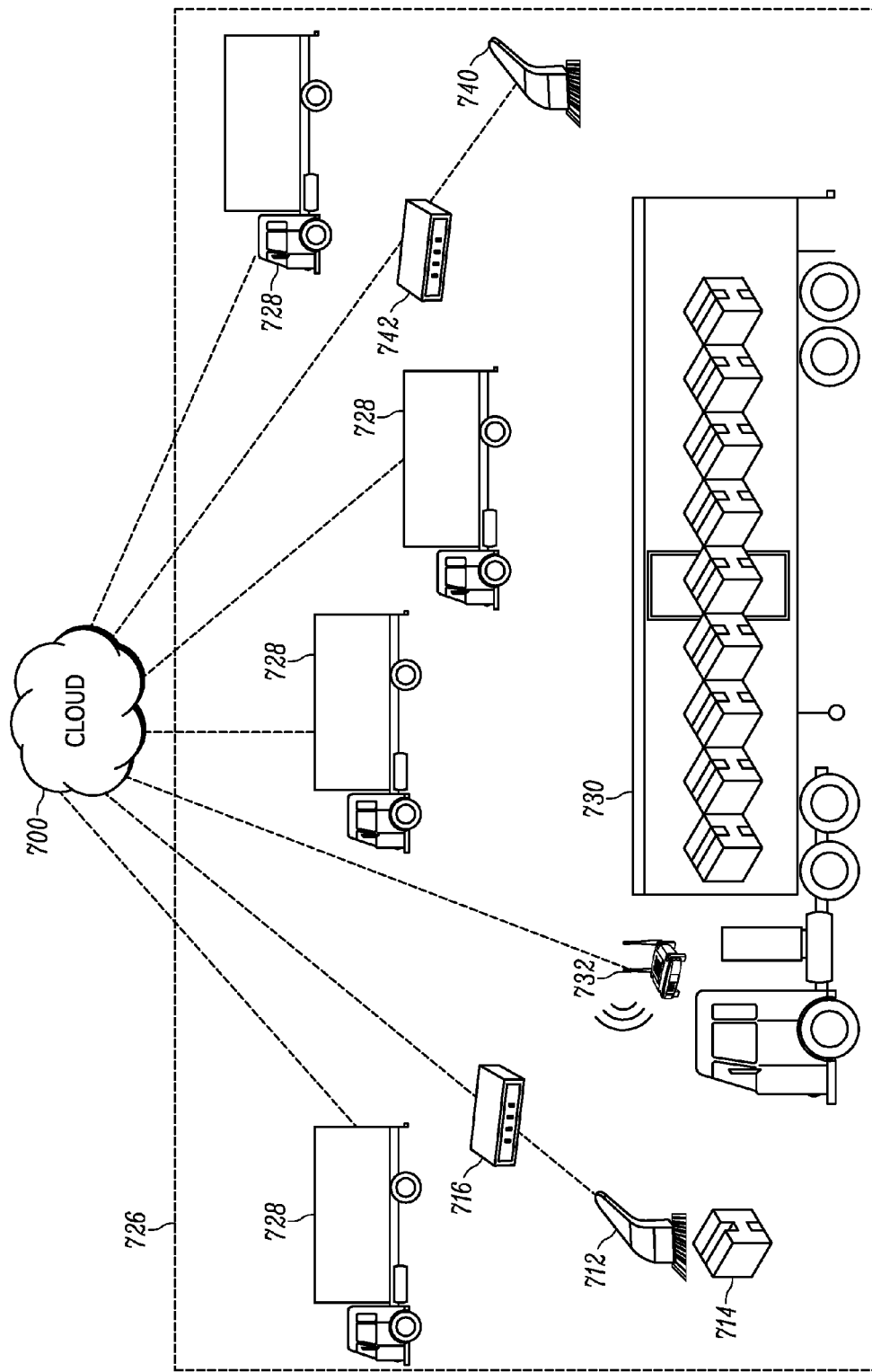

FIG. 7B depicts another set of devices associated with a carrier's world 726. Because the carrier's world 726 and the manufacturer's world 702 each communicate via a common device management infrastructure, embodiments may provide the ability to seamlessly transition devices and statuses from one world to the next. For example, the manufacturer's world 702 and the carrier's world 726 each include the barcode scanner 712 located at the manufacturer's shipping dock for scanning outgoing packages. As packages are scanned at the shipping dock, the barcode scanner 712 may report the scanned barcode via the gateway device 716 to notify the carrier that a new shipment is ready for transport.

The barcode scanner 712 and the gateway device 716 can be understood to be present in two worlds simultaneously, although the authority to administer these devices may be associated with their respective owner. As such, it should be readily appreciated that the contents of a particular world may be separate and distinct form the idea of device ownership, as one or more devices, applications, or the like may be present within a world even if the owner of the world is not authorized to administer the device itself.

The carrier's world 726 may include a plurality of shipping trucks 728, and a particular shipping truck 730 that is shipping the package 714 received from the manufacturer as described with respect to FIG. 7A. The particular shipping truck 730 may include one or more devices 732 that allow the particular shipping truck 730 to provide information via the cloud. For example, a GPS sensor on the particular shipping truck 730 may provide notifications of the location and speed of the truck using the device management infrastructure.

The carrier's world 726 may also include one or more barcode scanners 740 located at a merchant receiving dock. As shipments are delivered by the carrier, a barcode scanner owned by the merchant receiving the delivery may scan the incoming package and notify the carrier that the package has been delivered. Similarly to the barcode scanner at the loading dock 712, the merchant's barcode scanner 740 may be owned by the merchant and the carrier may be provided with access through the device management infrastructure.

Figure 7C:
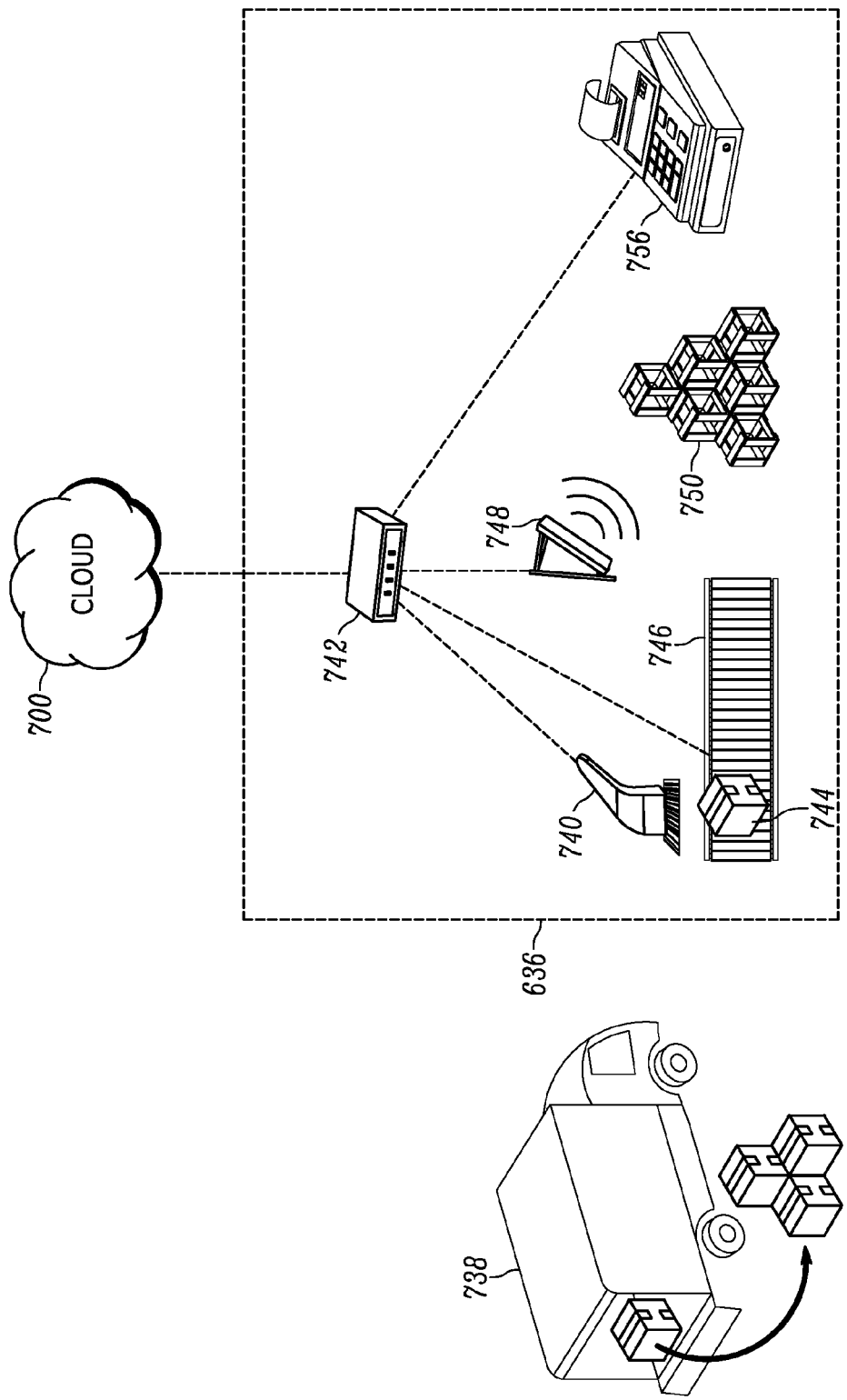

FIG. 7C depicts another set of devices associated with a merchant's world 736. As described with respect to the manufacturer's world 702, the merchant's world 736 may include one or more barcode scanners 740, RFID scanners 748, gateway devices 742, conveyor belts 746, and the like. As products are received from the carrier, a receiving dock barcode scanner 740 may scan the incoming products to confirm receipt. Incoming products 744 may be processed via the conveyor to be added to a product inventory 750, which is tracked via an RFID scanner 748. In some embodiments, the same RFID tag used to track the product at the manufacturer is also used to track the product in the merchant inventory 750. The merchant's world 736 may also include a point-of-sale 756. The point-of-sale 756 may scan products that are being sold to consumers. Each of the devices 740, 746, 748, 756 may be in communication with the device management infrastructure via the cloud 700. The device information provided by these devices may be converted into a device agnostic format by the gateway device 742 and used to track product inventory levels, manage shipping invoices, track customer purchase histories, and the like, using a device-agnostic communication format as described herein.

Figure 7D:
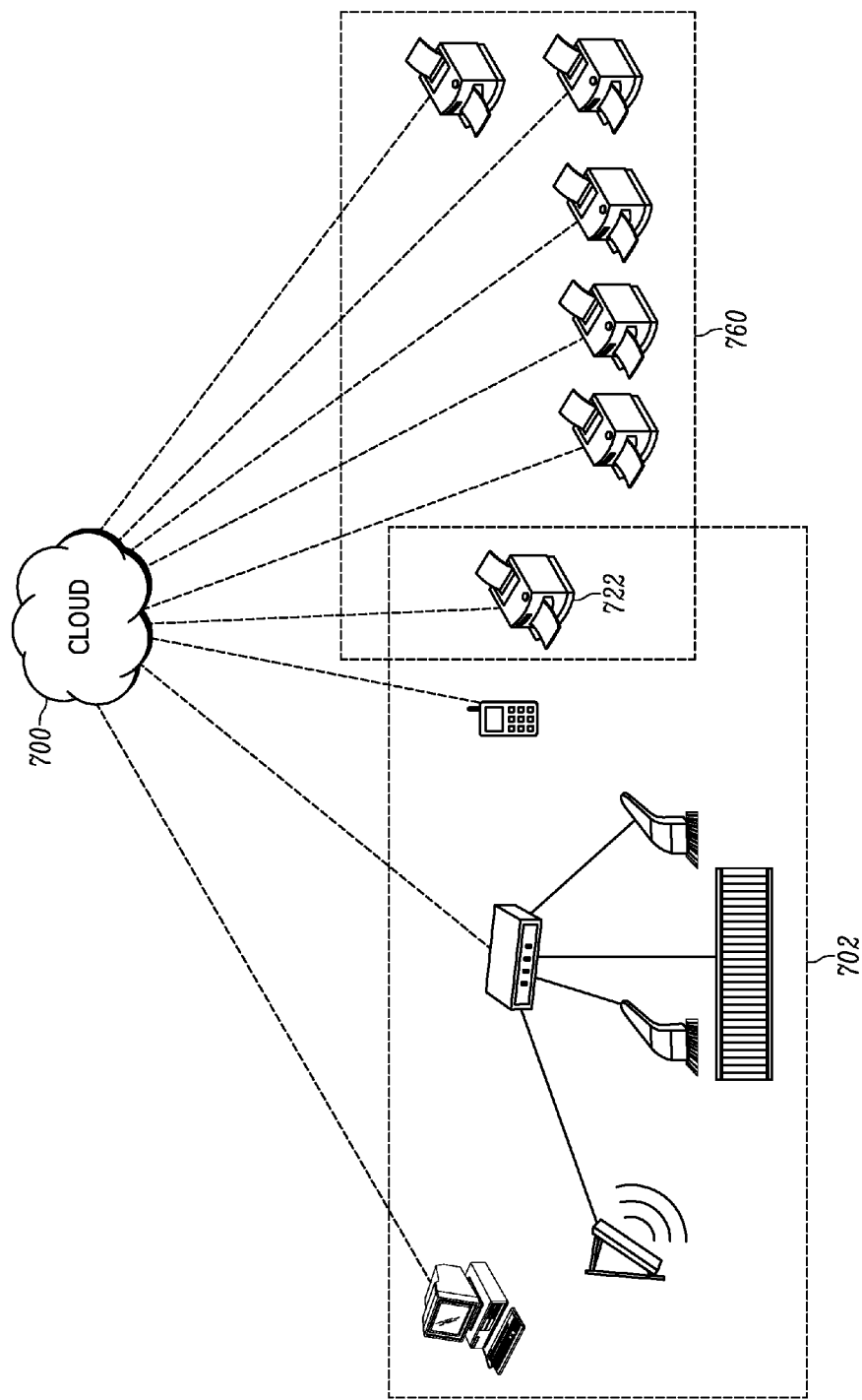

FIG. 7D depicts an example of a dynamically configurable groups and worlds in accordance with embodiments of the present invention. FIG. 7D depicts the manufacturer's world 702 described above and a servicer's world 760. The servicer's world corresponds to devices within the world of a printer maintenance service. As described above with respect to FIG. 6, devices, such as printers, may be dynamically associated with a particular group in response to certain conditions, such as an error state. In the present example, the printer 722 is both owned by the manufacturer, and experiencing an error condition. Since the manufacturer is the owner of the printer, the printer is located within the manufacturer's world 702. Since the printer is exhibiting an error state, and the manufacturer has configured the printer for dynamic access by the printer maintenance service, the printer 722 is also located within the servicer's world 760.

As such, both the manufacturer and servicer may have access to device information provided by the printer 722 through the device management infrastructure, as the printer is located within both worlds.

Example Inventory Management System

FIG. 8 illustrates an inventory system 800 for use in accordance with example embodiments of the present invention. For example, the inventory management system 800 might be implemented to track one or more product inventories 706 and 750 described with respect to FIGS. 7A and 7C, respectively. As described above, one use of a device management infrastructure involves managing a "smart" inventory system. Such an inventory system may be operable to track the presence and quantity of items within the inventory. The present example depicts two "rack" entities 804 and 806 in communication with a device management server 802. As described above, the device management server may be operable to communicate device information received from the rack entities 804 and 806 using a device management infrastructure. For example, the presence of inventory items reported by the rack entities 804 and 806 may be transmitted to a customer application server 808 to manage stock levels and product orders. The application server 808 may further report this information to customer devices 810 and 812. Although the present example is described with respect to a customer application server executing outside of the "cloud", it should be readily appreciated that the customer could also define applications to execute within the device management infrastructure to perform the same or similar functionality.

The rack entity 804 may include a plurality of individual devices. For example, the rack entity 804 may include multiple RFID antennae 816 in communication with one or more RFID readers 814. The RFID antennae 816 may detect and report the presence of particular RFID tags within a given location of the rack (e.g., a particular drawer). The RFID readers 814 may receive signals from the RFID antennae 816 and communicate the presence of particular tags to an edge box 818. The edge box 818 may function similarly to the device gateway described above with respect to FIGS. 1, 4, and 7 above. As described above, the edge box 818 may also execute one or more applications to analyze, process, or aggregate received data. For example, the edge box 818 may aggregate data from each RFID reader 814 to build a data structure describing the entire inventory status of the rack entity 804. This rack inventory data structure may be transmitted to the device management server 802, rather than reporting every tag reading from each RFID reader 814 separately.

It should also be appreciated that, despite the fact that the rack entity 804 contains several individual devices (e.g., multiple RFID readers and antennae, possibly multiple redundant edge boxes, etc.), the rack entity 804 may be represented by the device management infrastructure as a single virtual device model. In some embodiments, virtual device models may be presented in a hierarchical fashion, allowing the viewer to drill down to particular individual components as desired.

Example Device Management Infrastructure Interfaces

Figure 9:
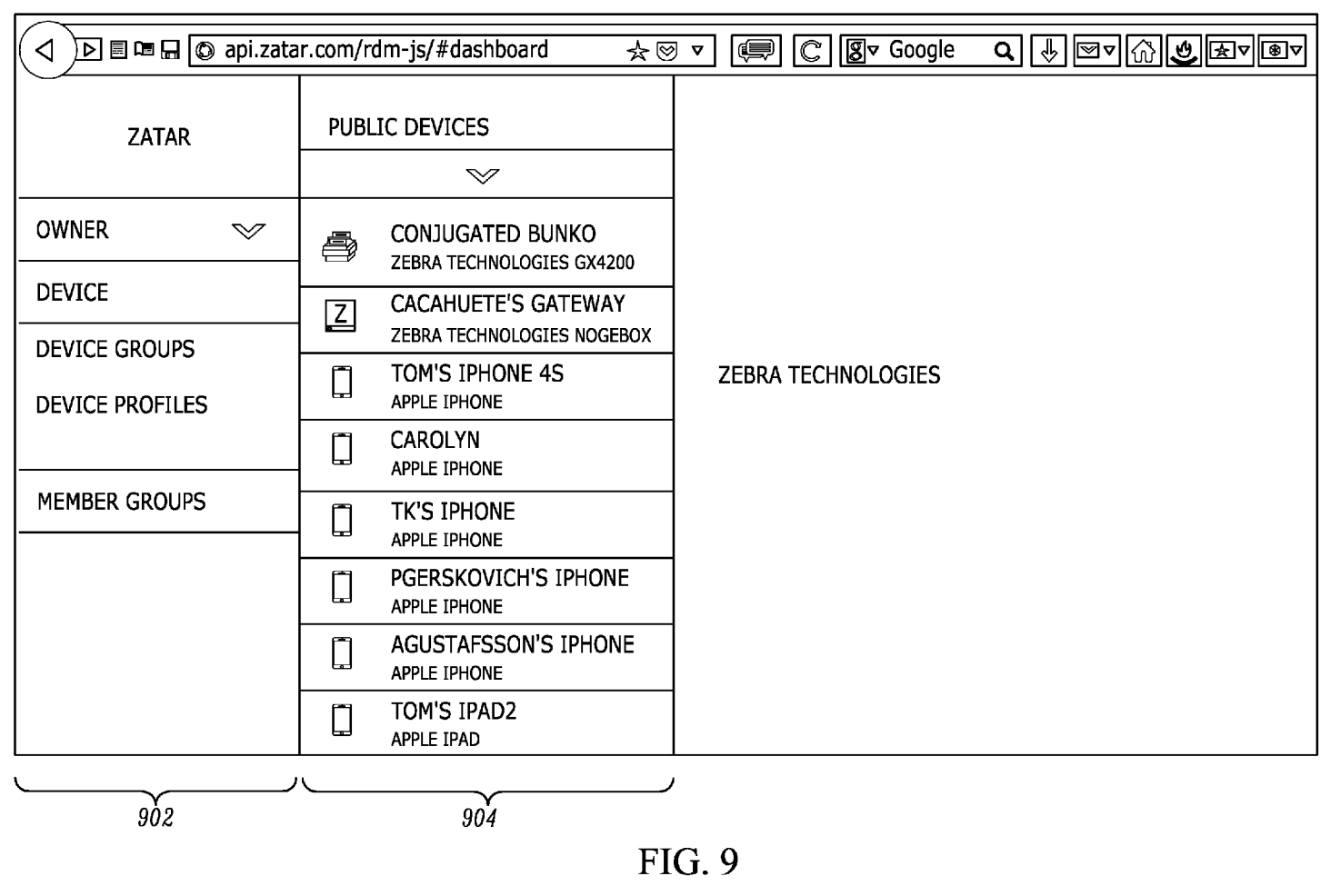

FIGS. 9-14 illustrate example interfaces for managing devices in accordance with example embodiments of the present invention. FIG. 9 illustrates an example user "dashboard" view that provides the user with access to one or more virtual device models representing devices in communication via the device management infrastructure. The left menu portion 902 includes several interface controls allowing the user to view, add, and edit devices to which the user has access. The left menu portion 902 may also allow the user to select from public or private devices, or a particular group of devices. Selection of a particular group of devices may populate a center menu portion 904 with interface controls that allow for selection of a particular device that is part of the group selected in the left menu portion 902. The left menu portion 902 may also include interface controls allowing the user to add a device, to create a device profile, to create or manage device groups, to invite another user to receive access to one or more of the user's devices, or the like.

Figure 10:

FIG. 10 depicts an example illustration of a visualization of a device virtual model, or "avatar" in accordance with embodiments of the present invention. The device virtual model may include a variety of types of information about the device, including the configuration of the device, readings from one or more sensors coupled to the device, and/or an activity log associated with the device. In some embodiments, the device virtual model may also include interface controls allowing one or more commands to be sent to the device (not shown). In the present example, the device is a "public" device, and as such is set with "read only" access permissions. It should be readily appreciated that a non-read only device could have interface controls to configure various aspects of the device, such as but not limited to device power management settings, device network settings, device troubleshooting tools, or the like.

Figure 11:

FIG. 11 depicts an example illustration of an "add device" menu in accordance with embodiments of the present invention. The add device menu may allow for the user to enable one or more devices to register with the device management infrastructure. Upon successful registration, the newly added device may be added to the user's dashboard/control panel (e.g., added to the user's "world"). New devices may be discovered according to various techniques. For example, a device may be preconfigured to communicate with the device management infrastructure, and providing the device serial number may register the device with the particular user account performing the "Add" operation. Additionally or alternatively, devices may be preconfigured to operate for a particular user at the time of manufacture or shipping. As yet another alternative or additional embodiment, devices may execute a registration of configuration application. For example, a smartphone may download an "app" that configures the smartphone to report device information to the device management infrastructure, and the "app" may request the account name of the user for registration. In some embodiments, the registered device may function as a gateway device enabling communication with one or more additional devices, which may also be added to the device management infrastructure in the same "Add" operation.

FIG. 12 depicts an alternative illustration of the "dashboard" view described above with respect to FIG. 9. FIG. 12 depicts a view in which device groups are displayed in a vertical column on the left side of the interface. Selection of a device group populates a column to the right of the leftmost column with icons for each device within the group. Selection of a particular device within the group displays the information associated with the device avatar (e.g., a display for the device as described above with respect to FIG. 10) in a portion of the interface to the right of the column with the device icons.

Figure 13:
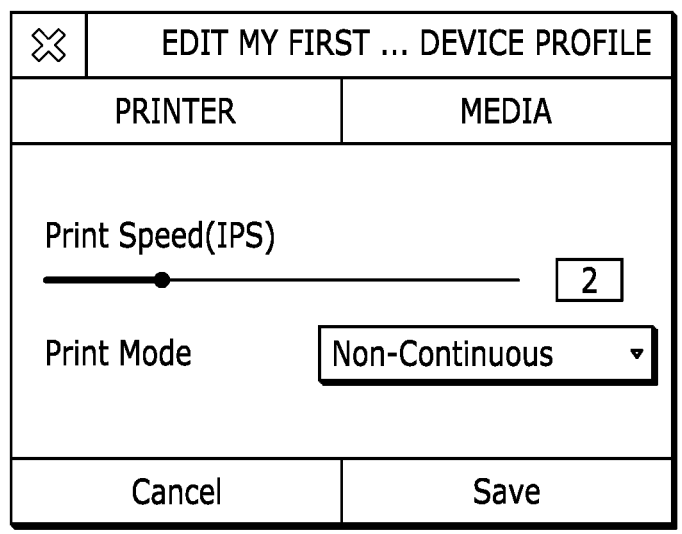

FIG. 13 depicts an example illustration of a device profile menu in accordance with embodiments of the present invention. The device profile menu may allow for a set of device settings to be saved for application to compatible devices in communication with the device management infrastructure. For example, the device profile menu depicted in FIG. 12 allows a user to specify a print speed and print mode for configuring a particular printer. The user may then select a compatible device or group of devices and apply the profile settings to each selected device via the user dashboard (see, e.g., FIG. 9). Various types of devices may include different profile settings. For example, a network router profile would typically not include settings for a print speed and print mode, while a printer profile would not include network Quality of Service (QoS) settings.

Figure 14:
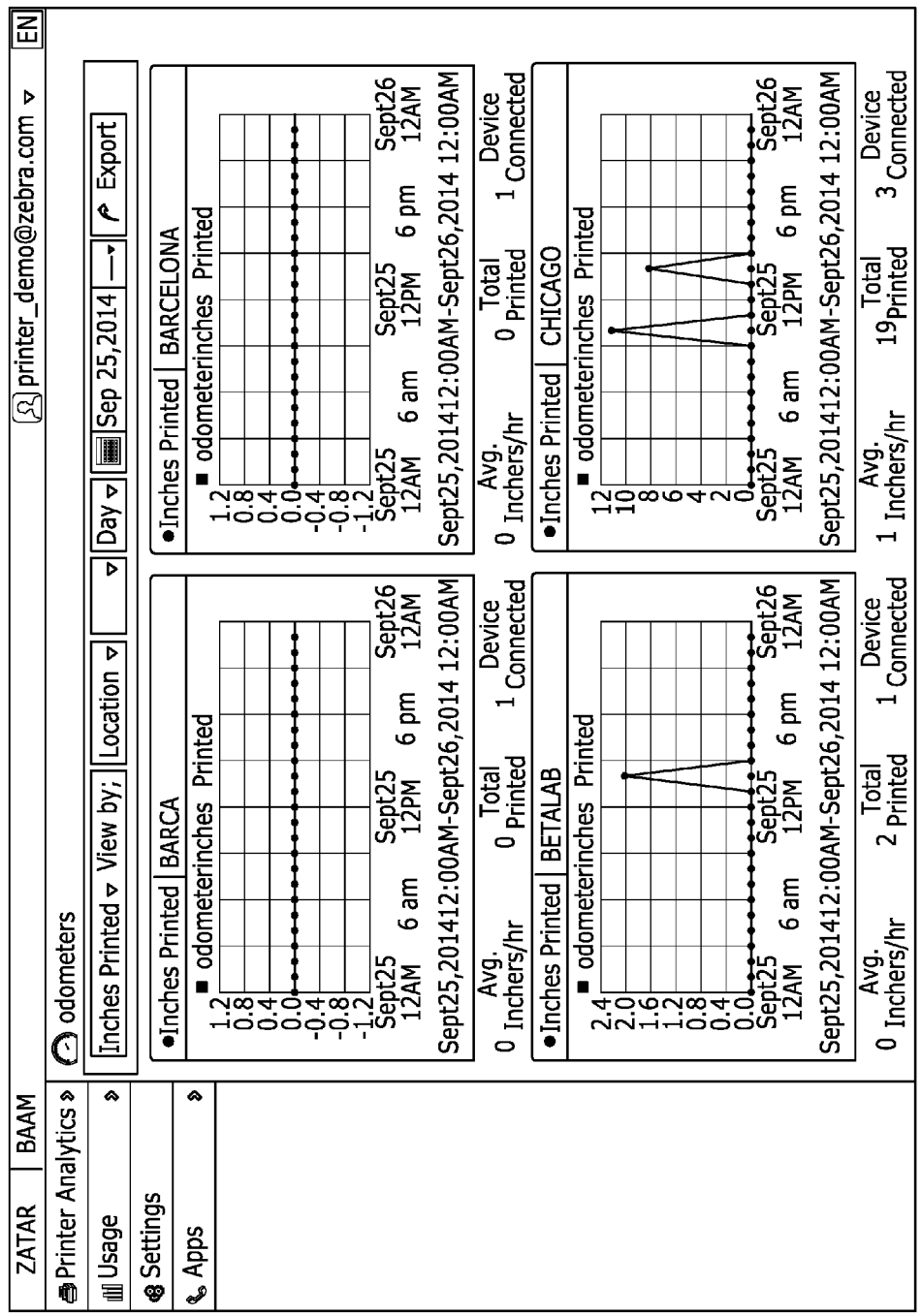

FIG. 14 depicts an example illustration of a device statistics menu in accordance with embodiments of the present invention. As described above, embodiments may provide the ability to aggregate and analyze data from individual devices, device groups, or the like. As a result of this aggregation and analysis, embodiments may provide with statistics related to the devices managed by the device management server. In some embodiments, statistics are provided for an individual device, or a particular group of devices. For example, statistics may be tracked and provided for an individual printer, all printers in a particular company office, or all printers across all company offices. Embodiments may advantageously leverage access to this data to provide a variety of data mining and analytic functions. For example, embodiments may track the mean time before failure for devices by identifying failure error conditions, embodiments may track the average lifespan of consumable materials (e.g., ink ribbons or cartridges) used by devices, or the like. In some embodiments, data may be electively provided by users/owners of devices to a public group or public repository, and statistics may be derived for all devices providing data to the public repository.

Example Operations Employing Device Management Infrastructure in Association with a Healthcare Information System FIG. 15 depicts an example embodiment that employs a device management infrastructure in conjunction with a healthcare information system to facilitate tracking of patient locations, capturing of timestamps related to patient locations, and calculating analytics based on tracked location data and captured timestamps. In particular, a patient location tracking system 1500 includes at least one beacon 1504 being worn, attached, or otherwise associated with a patient 1502. The beacon 1502 broadcasts a signal that may be detected by one or more detection devices 1506 positioned at particular locations within a healthcare organization. The detection devices 1506 communicate with a management server 1510 via a network 1508. The management server 1510 is a management server for enabling communications via a device management framework such as described above with respect to FIG. 1, element 102, FIG. 2A, element 200, FIG. 3, element 300, and FIG. 8, element 802. The management server 1510 provides information to one or more healthcare information systems 1512 to provide the healthcare information system 1512 with location information for the tracked patient 1502, along with timestamps of when the patient entered the particular location.

The detection device 1506 may communicate with one or more management servers 1510 via the network 1508. The network 1508 may be, for example, a wireless network provided by the healthcare organization. In some embodiments, the network 1508 includes a public wireless network provided by the healthcare organization for public user. In this manner, embodiments may provide patient location tracking via network systems that are already in place, without the need for new systems or software to be installed at the healthcare organization to facilitate communication between the beacon 1504, the detection device 1506, the management server 1510, and the healthcare information system 1512, beyond the installation of detection devices 1506.

The detection device 1506 may select particular beacons for use in a patient tracking operation by a variety of operations. For example, the detection device 1506 may filter particular signals (e.g., Bluetooth signals) for detection based on a type of device, a signal strength (e.g., to exclude devices that are likely not within a particular threshold distance of the detection device 1506), whether the beacon 1504 is registered with the management server 1510 or the detection device 1506, whether the beacon 1504 is indicated as inactive or active by the management server 1510, or the like.

The detection device 1506 may be configured to communicate with the network 1508 via a variety of network communication protocols, such as public Wi-Fi networks, private Wi-Fi networks, Bluetooth, 3G, 4G LTE, and the like. In some embodiments, the detection device 1506 may be configured to communicate according to each of a public Wi-Fi network (e.g., a wireless network offered by a healthcare organization that is accessible to the general public, visitors, and the like), a private Wi-Fi network (e.g., a wireless network that is only accessible to authorized users associated with the healthcare organization), and by a cellular data network in order to increase the likelihood that the detection device will be able to provide information to the management server in a variety of scenarios depending upon the different types of connectivity available.

Embodiments may facilitate the tracking of patients as they enter the healthcare organization and proceed through treatment. In one particular example, the patient 1502 is provided with the beacon 1504 (e.g., a BLE beacon embedded in a wristband) when the patient is picked up in an ambulance, when the patient enters the emergency room, or upon another initial contact with the healthcare organization. At the time the patient receives the beacon, an association is made between the particular patient and the particular beacon. The association may be made at various times during the registration process. In some embodiments, the association is made after the registration process has been completed, such as where the registration process involves time-sensitive procedures (e.g., cardiology unit patient intake). In some embodiments, the association between the patient and the beacon is performed within the healthcare information system 1512, and patient information is not exposed to the other components of the system.

At the patient proceeds through admission, registration, treatment, and other interactions with the healthcare organization, detection devices 1506 (e.g., tablet computers capable of communicating with a device management infrastructure as described herein) detect the beacon when the patient enters into a detection radius about the detection device 1506. For example, a given healthcare organization may include detection devices positioned in ambulances, in the emergency room, a catheterization room, at the admissions desk, within an initial nurse triage area, within a medical imaging laboratory, within an operating room, or at various other locations. As the patient enters the detection radius about each detection device, the detection device identifies the time and an identifier broadcast by the beacon, and reports the time and the identifier to the management server 1510. The management server 1510 may forward this information to the healthcare information system 1512, or the management server 1510 may analyze the data locally to determine analytics related to the patient's location and the time at which they entered the location. In some embodiments, the information is provided as an output file, an output message, or a printed output.

The detection device 1506 may also be operable to provide real-time feedback throughout the patient tracking and/or registration process. For example, the management server 1510 may send information to the detection device 1506 indicating the total time since patients located proximate to the detection device 1506 have begun the intake or registration process, or identifiers for all patients associated with beacons that are detected within a threshold distance of the detection device 1506. In yet further embodiments, an elapsed time since the beacon 1504 entered into proximity with the detection device is displayed, to indicate how long the patient has been in a particular location. In additional embodiments, the detection device 1506 may display messages received from the management server 1510, other detection devices, or the like.

One particular use for such an infrastructure involves tracking the time between initial registration of patients and the start of treatment. Some treatment protocols dictate a particular time period between when the patient is first seen, and the time at which treatment should begin (e.g., 90 minutes from registration to treatment for patients requiring revascularization of coronary arteries). Embodiments as described herein provide a method for tracking this time automatically, for measuring the time which patients spend at particular locations in the registration and treatment process, and for identifying bottlenecks and delays in the process. Healthcare organizations may thus employ a system as described herein to improve their data tracking to gather accurate metrics for evaluating whether they are meeting the requirements of the treatment protocol. In some embodiments, specific locations are associated with beginning a timer (e.g., a starting point) and other locations are associated with stopping the timer or tracking a time since the start of the timer (e.g., one or more finish lines). In some embodiments, particular detection devices 1506 are configured to function to either start or stop one or more of the timers.

Embodiments may leverage the use of "off the shelf" devices as the detection devices 1506. Such devices may be configured to communicate with a device management infrastructure as described above with respect to FIGS. 1-14. For example, tablet computers may be configured with Bluetooth technology for communication with beacons 1504, and wireless capability and appropriate software to communicate with a device management infrastructure. In this manner, such tablets may be distributed throughout the healthcare organization and registered at particular locations, such that when the patient is within the detection radius of each tablet, the patient's beacon identifier and the current time is reported by the tablet to the management server 1510.

FIG. 16 illustrates an example of a patient location tracking system employing a plurality of detection devices 1604, 1606, 1608, 1610. In the present example, the detection devices 1604, 1606, 1608, and 1610 are located within an emergency room entrance, at a registration desk, within a cardiology unit, and within an operating room, respectively. As the patient 1602 enters the emergency room, the presence of the patient's beacon is detected and reported to a management server 1614 via a network 1612. As noted above, communication with the management server 1614 may be performed via a device management infrastructure as described above with respect to FIGS. 1-15.

As the patient 1602 moves throughout the healthcare organization, the patient's location is tracked by the beacon communicating with each detection device. At the time of the beacon's detection, the detection device also communicates a timestamp of the detection to the management server 1614. The management server 1614 is in communication with one or more healthcare information systems 1616 to provide data related to the patient locations and captured time stamps. The management server 1614 may provide the data as an exported file that includes detection events (e.g., entry and exit to areas associated with particular detection devices, start/stop events associated with timers based on detection events, etc.) and timer events (e.g., overall elapsed time and/or the state of one or more timers associated with the detection events). In some embodiments, the healthcare information system 1616 may employ an algorithm or otherwise process the data to identify an earliest event associated with a particular beacon at each location.

Data may be provided to the healthcare information system 1616 in a variety of manners. For example, in some embodiments an application executing on the management server 1614 analyzes received data and provides formatted output relating to the time spent at particular locations by particular patients. Such formatted output may also include an analysis of which locations are causing the most delay in the treatment process, the delay associated with particular locations as compared to an expected delay for each location, or the like. In other embodiments, the management server 1614 may provide raw data (e.g., only beacon identifiers, time stamps, and identification of particular locations) to the healthcare information system 1616 to reduce the amount of private patient data exposed via the device management infrastructure.

To enable a detection device 1604, 1606, 1608, 1610 to perform detection of beacons as described herein, the detection device may be registered with the management server 1614. For example, an administrator or other user may execute software to notify the management server 1614 of the presence of the detection device, the location at which the detection device is positioned, and the like. The detection device may also receive application software for detection of beacons, capturing of timestamps, and reporting as such to the management server 1614. In some embodiments, the detection device may be unaware of its assigned location (e.g., in the emergency room, operating room, registration desk, etc.), and the management server 1614 may associate a unique identifier of the detection device with a particular location within the healthcare organization based on data stored locally to the management server 1614 and unavailable to the detection device. In some embodiments, the detection devices 1604-1610 may include a capture threshold (e.g., a minimum signal strength to identify a beacon as detected), a release threshold (e.g., a signal strength at which the beacon is identified as no longer detected by the detection device), a scanning mode (e.g., a scanning frequency or the like), and/or a scanning interval (e.g., how often the detection device identifies nearby beacons). In some embodiments, the detection devices 1604-1610 may also include a list of beacon identifiers for beacons registered with the patient location tracking system. Such a list may be provided by the management server 1614. In some embodiments, a time synchronization server may be used to synchronize one or more of the detection devices with one another and/or with the management server.

Example Device Management Module Operations

Turning now to FIG. 17, example operations for device management parameters are illustrated from the perspective of a device management server. The operations illustrated in FIG. 17 may, for example, be performed by the device management system 104 and/or the device management server 102, with the assistance of, and/or under the control of one or more devices, such as the apparatus 200, and may use the processor 202, the memory 204, the input/output module 206, the communications module 208, and the device management server 210.

In operation 1702, the apparatus 200 includes means, such as input/output module 206, communications module 208, or the like, for receiving device information from one or more devices. This device information may be retrieved or received from one or more edge devices as described with respect to FIG. 1. It should be appreciated that although the instant example is described with respect to receiving device information from a device, device information may also be received and processed in a similar manner from other entities configured to communicate with the device management infrastructure (e.g., applications executing within the infrastructure or external systems communicating via an API). Routing of information may be determined by adding the device information to a representation of the device (e.g., a virtual device model object). Access to the representation of the device may be provided to other entities within the device management infrastructure based on the configuration of the representation of the device (e.g., permission settings, whether particular applications are executing and have access to the representation, etc.).

In operation 1704, the apparatus includes means, such as the processor 202, to determine a set of permissions for the device associated with the device information. For example, as described above, the device management infrastructure may include a permissions database 106 indicating how data for particular devices should be routed.

In operation 1706, the apparatus includes means, such as the processor 202 or credentialing circuitry 212, to identify one or more receivers for the device information based on the set of permissions. For example, the permissions may define one or more rules for the routing of data. These rules may include routing to different receivers based on the type of data, such as routing certain types of data (e.g., printer consumable levels) to a first receiver, and other types of data (e.g., data on the contents that the printer is printing) to a second receiver. In some embodiments, these rules may include alterations to the device permissions status (e.g., assigning the device to a different group) based on the content of the device information (e.g., placing the printer in a group accessible to a maintenance service in response to detection of an error condition on the printer). It should be appreciated that the receiver can include another device, a particular user dashboard, a particular application or applications executing within the device management infrastructure, a group of devices, an application or system external to the device management infrastructure, or the like.

At action 1708, the device information is provided to the determine receiver. Providing the device information may include transmitting the device information to the particular receiver, placing the information in a transmission queue, sending a message external to the device management infrastructure, sending the device information via an API, or the like.

FIG. 18 illustrates a signal diagram of an example method for establishing communications between a legacy device and a device management infrastructure via a gateway device, such as the apparatus 218 described with respect to FIG. 2B or the gateway device 400 described with respect to FIG. 4. At action 1802, a legacy device provides a set of device information to a gateway device in a device-native format. At action 1804, the gateway device converts the device information from the device-native format to a device-agnostic format (e.g., a JSON object) and, at action 1806, transmits the device-agnostic device information to a remote server. At action 1808, the remote server processes the device information. Processing of the device information may include providing the device information to one or more applications, executing a command contained within the device information, updating a virtual device model associated with the legacy device based on the device information, or the like. At action 1810, the remote server sends a device command to the legacy device via the gateway device. For example, the device command may be to alter the configuration of the legacy device, to perform an action (e.g., to print a label or laminate a document), or any other command. The device command may also be encoded in a device-agnostic format. At action 1812, the gateway device receives the device command and coverts it to the device-native format. At action 1814 the gateway device transmits the device command in the device-native format to the legacy device. At action 1816, the legacy device receives the device command in the device-native format and executes the command.

Example Operations for Use in a Healthcare Organization Patient Tracking System

FIG. 19 illustrates a process 1900 for utilizing a device management infrastructure for beacon tracking and time stamp capturing in accordance with some embodiments of the present invention. The process 1900 provides a mechanism for detecting the locations of beacons along with particular time stamps, such as for use in a patient tracking system as described above with respect to FIGS. 15 and 16. The process 1900 may, for example, be performed by a detection device 1506 as described above with respect to FIG. 15, or elements of the device management system 104 and/or the device management server 102, with the assistance of, and/or under the control of one or more devices, such as the apparatus 200, and may use the processor 202, the memory 204, the input/output module 206, the communications module 208, and the device management server 210.

At action 1902, a registration of a beacon with the system is received. Registration of a beacon may be performed at various times. For example, in some embodiments a plurality of beacons are initially registered with the system, where the particular identifiers associated with those beacons are pre-stored in the system prior to any patient tracking operations. In some embodiments, beacons are registered at the time they are provided to a patient to begin the patient tracking process. In some embodiments, beacons are registered upon first detection by the system, such that detection and registration are performed simultaneously. Registration may be accompanied by other tasks related to patient intake, such as entering patient information into a healthcare information system during the admission process. Registration of the beacon may be associated with a particular patient record in the healthcare information system (e.g., storing the beacon identifier in the patient's medical records or within a hospital ADT system). In some embodiments, tracking of the beacon may not be enabled until the beacon is registered. In some embodiments, registration includes registering the detection device with the device management infrastructure as described above with respect to FIGS. 1-14.

Beacons may be activated and registered as active beacons prior to being provided to the healthcare system. In such cases, all beacons may be in an active or transmitting state when they are received by the healthcare system. Such beacons may be packaged in packaging that includes an electromagnetic shielding component (e.g., a Faraday cage), such that the beacons are not detected by the detection devices until removed from the packaging. In other embodiments, beacons may be registered with the patient location system but placed in a "sleep" mode. Once removed from the packaging, the beacon may exit sleep mode (e.g., upon receiving an activation signal, upon a user physically manipulating the beacon, or the like).

At action 1904, the presence of the beacon is detected at a particular location by a detection device. As described above, detection devices may be associated with and/or positioned at particular locations within the healthcare organization, such that detection of a beacon by a particular device is indicative of the fact that the beacon is within that particular location. In this manner, detection devices may employ detection protocols that have a limited radius to minimize the chance of overlap in detection by multiple devices or false detection by detection devices in other locations. For example, detection devices and beacons may employ the BLE protocol. Settings associated with the detection devices may be used to associate detection by a particular detection device with a particular event (e.g., entry, exit, starting a timer, stopping a timer, or the like).

At action 1906, a timestamp is calculated at the time the presence of the beacon is detected. The timestamp may be calculated by an internal clock of a detection device, or by a remote server (e.g., a management server) at the time the detection is reported. In some embodiments, the timestamp is provided via a public or private time reference server. For example, embodiments may utilize a network time protocol (NTP) server operated by a healthcare organization or a public NTP server.

At action 1908, the location at which the beacon was detected and the determined timestamp are stored. As noted above, these functions may be performed by either the detection device or the management server. For example, in some embodiments the detection device may report its own location and a timestamp calculated by the detection device to the management server, while in other embodiments the management server may receive only a beacon identifier from the detection device and determine the location based on a stored location of the detected device and determine the timestamp based on the time at which the beacon identifier was received from the detection device.

FIG. 20 illustrates a flow diagram of an example process 2000 for tracking registration times in a healthcare setting using a device management infrastructure in communication with a healthcare information system in accordance with some embodiments of the present invention. As noted above with respect to FIGS. 15-16 and 19, embodiments may advantageously assist with storing and tracking registration times and other analytics related to patient treatment using a device management infrastructure as described herein. The process 2000 illustrates one example of a process for performing these functions using a management server of such a device management infrastructure. The process 2000 may, for example, be performed by the device management system 104 and/or the device management server 102, with the assistance of, and/or under the control of one or more devices, such as the apparatus 200, and may use the processor 202, the memory 204, the input/output module 206, the communications module 208, and the device management server 210.

At action 2002, an initial time stamp and location at which a beacon was detected are received via a device management infrastructure. As described above, it should be appreciated that, while the instant example describes receiving a location, a timestamp, and beacon identifier, other embodiments may only receive a beacon identifier, a beacon identifier and a time stamp, a beacon identifier and a location, or various additional and alternative combinations and additional sets of data. The detection device may provide the data via the device management infrastructure according to the various methods, systems, and protocols (e.g., as JSON object) as described above with respect to FIGS. 1-16.

At action 2004, upon receiving the initial location of the beacon (e.g., the patient's presence at a registration desk or waiting area), a registration timer is started. At action 2006, a subsequent time stamp and location are received for a different location. Upon receiving the time stamp and different location, the registration timer is terminated at action 2008, as the detection of the beacon at the second location (e.g., the start of treatment) implies that registration has been completed.

At action 2010, the total time for registration is calculated based on the value of the registration timer. The total registration time may be used as an analytic to compare against a specified treatment protocol (e.g., 90 minutes for coronary artery revascularization). The calculated registration time may be reported to a healthcare information system via the device management infrastructure at action 2012. The calculated time may also be provided to the detection devices for local display via a display of the detection devices.

As will be appreciated, computer program code and/or other instructions may be loaded onto a computer, processor or other programmable apparatus's circuitry to produce a machine, such that execution of the code on the machine by the computer, processor, or other circuitry creates the means for implementing various functions, including those described herein.

As described above and as will be appreciated based on this disclosure, embodiments of the present invention may be configured as methods, mobile devices, backend network devices, and the like. Accordingly, embodiments may comprise various means including entirely of hardware or a combination of software and hardware. Furthermore, embodiments may take the form of a computer program product on at least one computer-readable storage medium having computer-readable program instructions (e.g., computer software) embodied in the storage medium. Any suitable computer-readable storage medium may be utilized, including non-transitory hard disks, CD-ROMs, flash memory, optical storage devices, magnetic storage devices, or the like.

Embodiments of the present invention have been described above with reference to block diagrams and flowchart illustrations of methods, apparatuses, systems and computer program products. It will be understood that each block of the circuit diagrams and process flowcharts, and combinations of blocks in the circuit diagrams and process flowcharts, respectively, can be implemented by various means including computer program instructions. These computer program instructions may be loaded onto a general purpose computer, special purpose computer, or other programmable data processing apparatus to produce a machine, such that the computer program product includes the instructions which execute on the computer or other programmable data processing apparatus create a means for implementing the functions specified in the flowchart block or blocks.

These computer program instructions may also be stored in a computer-readable storage device that can direct a computer or other programmable data processing apparatus to function in a particular manner, such that the instructions stored in the computer-readable storage device produce an article of manufacture including computer-readable instructions for implementing the function discussed herein. The computer program instructions may also be loaded onto a computer or other programmable data processing apparatus to cause a series of operational steps to be performed on the computer or other programmable apparatus, thereby producing a computer-implemented process such that the instructions executed on the computer or other programmable apparatus cause performance of the steps and thereby implement the functions discussed herein.

Accordingly, blocks of the block diagrams and flowchart illustrations support combinations of means for performing the specified functions, combinations of steps for performing the specified functions and program instruction means for performing the specified functions. It will also be understood that each block of the circuit diagrams and process flowcharts, and combinations of blocks in the circuit diagrams and process flowcharts, can be implemented by special purpose hardware-based computer systems that perform the specified functions or steps, or combinations of special purpose hardware and computer instructions.

Many modifications and other embodiments of the inventions set forth herein will come to mind to one skilled in the art to which these embodiments of the invention pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for tracking beacons utilizing a device management infrastructure, the method comprising:
    registering, by a device management server, at least a first detection device associated with a first location and a second detection device associated with a second location with a device management infrastructure;
    setting a first sensitivity level of the first detection device to a first value based on first expected movement of beacons at the first location;
    setting a second sensitivity level of the second detection device to a second value based on second expected movement of beacons at the second location, the first value being different than the second value due to a difference between the first expected movement and the second expected movement;
    receiving, via the device management infrastructure and from the first detection device, a beacon identifier associated with a beacon detected by the first detection device;
    storing a first time stamp associated with detection of the beacon by the first detection device;
    receiving, via the device management infrastructure and from the second detection device, the beacon identifier associated with the beacon as detected by the second detection device;
    determining, based on the first time stamp and a second time stamp associated with detection of the beacon by the second detection device, an elapsed time between detection of the beacon by the first detection device and detection of the beacon by the second detection device; and
    reporting the elapsed time to a healthcare information system.

2. The method of claim 1, wherein the beacon comprises a wristband provided to a patient of a healthcare organization associated with the healthcare information system.

3. The method of claim 1, wherein the first location is a hospital registration desk and the second location is a hospital treatment room.

4. The method of claim 1, wherein the beacon is a Bluetooth Low Energy (BLE) beacon.

5. The method of claim 1, wherein the first detection device and the second detection device are tablet computers.

6. The method of claim 5, wherein the tablet computers are configured to communicate with a management server via a device management infrastructure.

7. The method of claim 6, wherein the tablet computers communicate with the device management infrastructure via a wireless Internet connection.

8. The method of claim 7, wherein the wireless Internet connection comprises a publicly available wireless connection provided by a healthcare organization, a private wireless connection provided by the healthcare organization, and a cellular network.

9. The method of claim 1, further comprising providing the elapsed time to the second detection device for display on a display coupled to the second detection device.

10. An apparatus for tracking beacons utilizing a device management infrastructure, the apparatus comprising:
    a device management server configured to:
        register at least a first detection device associated with a first location and a second detection device associated with a second location with a device management infrastructure, the first detection device having a first sensitivity level based on first expected movement of beacons at the first location, the second detection device having a second sensitivity level based on second expected movement of beacons at the second location, the first sensitivity level being different than the second sensitivity level;
        receive, via the device management infrastructure and from the first detection device, a beacon identifier associated with a beacon detected by the first detection device;
        store a first time stamp associated with detection of the beacon by the first detection device;
        receive, via the device management infrastructure and from the second detection device, the beacon identifier associated with the beacon as detected by the second detection device;
        determine, based on the first time stamp and a second time stamp associated with detection of the beacon by the second detection device, an elapsed time between detection of the beacon by the first detection device and detection of the beacon by the second detection device; and report the elapsed time to a healthcare information system.

11. The apparatus of claim 10, wherein the beacon comprises a wristband provided to a patient of a healthcare organization associated with the healthcare information system.

12. The apparatus of claim 10, wherein the first location is a hospital registration desk and the second location is a hospital treatment room.

13. The apparatus of claim 10, wherein the beacon is a Bluetooth Low Energy (BLE) beacon.

14. The apparatus of claim 10, wherein the first detection device and the second detection device are tablet computers.

15. The apparatus of claim 14, wherein the tablet computers are configured to communicate with a management server via a device management infrastructure.

16. The apparatus of claim 15, wherein the tablet computers communicate with the device management infrastructure via a wireless Internet connection.

17. The apparatus of claim 16, wherein the wireless Internet connection comprises a publicly available wireless connection provided by a healthcare organization, a private wireless connection provided by the healthcare organization, and a cellular network.

18. The apparatus of claim 10, wherein the device management server is further configured to provide the elapsed time to the second detection device for display on a display coupled to the second detection device.

* * * * *